US011633149B2

(12) United States Patent
Sanchez et al.

(10) Patent No.: US 11,633,149 B2
(45) Date of Patent: Apr. 25, 2023

(54) SYSTEMS AND METHODS FOR IMAGING AND MEASUREMENT OF SARCOMERES

(71) Applicant: Enspectra Health, Inc., Mountain View, CA (US)

(72) Inventors: Gabriel Sanchez, Menlo Park, CA (US); Fred Landavazo, IV, East Palo Alto, CA (US); Scott Delp, Stanford, CA (US); Kathryn Montgomery, Mountain View, CA (US)

(73) Assignee: ENSPECTRA HEALTH, INC., Mountain View, CA (US)

( * ) Notice: Subject to any disclaimer, the term of this patent is extended or adjusted under 35 U.S.C. 154(b) by 467 days.

(21) Appl. No.: 16/662,830

(22) Filed: Oct. 24, 2019

(65) Prior Publication Data

US 2020/0196938 A1 Jun. 25, 2020

Related U.S. Application Data

(63) Continuation of application No. PCT/US2018/030011, filed on Apr. 27, 2018.
(Continued)

(51) Int. Cl.
*A61B 5/00* (2006.01)

(52) U.S. Cl.
CPC .......... *A61B 5/4519* (2013.01); *A61B 5/0048* (2013.01); *A61B 5/0071* (2013.01); *A61B 5/0079* (2013.01); *A61B 5/6848* (2013.01)

(58) Field of Classification Search
CPC ............... A61B 5/4519; A61B 5/0048; A61B 5/0071; A61B 5/0079; A61B 5/6848;
(Continued)

(56) References Cited

U.S. PATENT DOCUMENTS 2,189,298 A 2/1940 Kurt et al.
3,655,259 A 4/1972 Miyauchi et al.
(Continued)

FOREIGN PATENT DOCUMENTS

AT 257294 T 1/2004
AU 4145801 A 8/2001
(Continued)

OTHER PUBLICATIONS

EP12853081.3 Examination Report dated Mar. 27, 2020.
(Continued)

*Primary Examiner* — Sean D Mattson

(74) *Attorney, Agent, or Firm* — Wilson Sonsini Goodrich & Rosati

(57) ABSTRACT

The present disclosure provides methods and apparatuses for identifying and/or analyzing a muscle tissue of a subject. An apparatus for identifying and/or analyzing muscle tissue of the present disclosure may comprise an optical element comprising an excitation probe and a collection probe. A method for identifying or analyzing muscle tissue of the present disclosure may comprise the generation of images of a muscle tissue using signals generated from the tissue by a beam of light directed towards the muscle tissue from the excitation probe and collected by the collection probe. Signals collected by the collection probe may include forward second harmonic generation signals.

21 Claims, 27 Drawing Sheets

Related U.S. Application Data

(60) Provisional application No. 62/491,868, filed on Apr. 28, 2017.

(58) Field of Classification Search
CPC .............. A61B 5/0082; A61B 5/7246; A61B 5/0062; A61B 5/0068; A61B 5/0073; A61B 5/0075; A61B 2576/02; G16H 30/40

See application file for complete search history.

(56) References Cited

U.S. PATENT DOCUMENTS

| | | | |
|---|---|---|---|
| 4,270,843 A | 6/1981 | Goto | |
| 4,416,519 A | 11/1983 | Kobayashi | |
| 4,515,444 A | 5/1985 | Prescott et al. | |
| 4,570,641 A | 2/1986 | Lieber et al. | |
| 4,598,715 A | 7/1986 | Machler et al. | |
| 4,693,606 A | 9/1987 | Podolsky et al. | |
| 5,056,530 A | 10/1991 | Butler et al. | |
| 5,093,719 A | 3/1992 | Prescott | |
| 5,159,402 A | 10/1992 | Ortiz, Jr. | |
| 5,161,063 A | 11/1992 | Krill et al. | |
| 5,181,511 A | 1/1993 | Nickolls et al. | |
| 5,225,676 A | 7/1993 | Matsuya | |
| 5,361,166 A | 11/1994 | Atkinson et al. | |
| 5,414,561 A | 5/1995 | Wakimoto et al. | |
| 5,457,576 A | 10/1995 | Atkinson et al. | |
| 5,880,465 A | 3/1999 | Boettner et al. | |
| 5,929,985 A | 7/1999 | Sandison et al. | |
| 5,987,346 A * | 11/1999 | Benaron ............... | A61B 5/1459 600/475 |
| 5,991,090 A | 11/1999 | Strahle | |
| 6,032,071 A | 2/2000 | Binder | |
| 6,198,834 B1 | 3/2001 | Belk et al. | |
| 6,208,886 B1 | 3/2001 | Alfano et al. | |
| 6,405,070 B1 | 6/2002 | Banerjee | |
| 6,485,413 B1 | 11/2002 | Boppart et al. | |
| 6,542,665 B2 | 4/2003 | Reed et al. | |
| 6,546,278 B2 | 4/2003 | Walsh | |
| 6,571,118 B1 | 5/2003 | Utzinger et al. | |
| 6,580,941 B2 | 6/2003 | Webb et al. | |
| 6,639,674 B2 | 10/2003 | Sokolov et al. | |
| 6,643,071 B2 | 11/2003 | Schnitzer | |
| 6,697,652 B2 | 2/2004 | Georgakoudi et al. | |
| 6,760,112 B2 | 7/2004 | Reed et al. | |
| 6,766,184 B2 | 7/2004 | Utzinger et al. | |
| 6,785,471 B2 | 8/2004 | Lee et al. | |
| 6,795,199 B2 | 9/2004 | Suhami | |
| 6,839,483 B2 | 1/2005 | Reed et al. | |
| 6,839,586 B2 | 1/2005 | Webb | |
| 6,889,075 B2 | 5/2005 | Marchitto et al. | |
| 6,912,412 B2 | 6/2005 | Georgakoudi et al. | |
| 6,967,725 B2 | 11/2005 | Denk et al. | |
| 7,091,500 B2 | 8/2006 | Schnitzer | |
| 7,307,774 B1 | 12/2007 | Schnitzer et al. | |
| 7,336,988 B2 | 2/2008 | Schnitzer | |
| 7,336,990 B2 | 2/2008 | Genet et al. | |
| 7,414,729 B2 | 8/2008 | Xie et al. | |
| 7,485,100 B2 | 2/2009 | Garcia-Webb et al. | |
| 7,616,986 B2 | 11/2009 | Seibel et al. | |
| 7,702,381 B2 | 4/2010 | Gaeta et al. | |
| 8,068,899 B2 | 11/2011 | Llewellyn et al. | |
| 8,259,167 B2 | 9/2012 | Ishiwata et al. | |
| 8,380,268 B2 | 2/2013 | Georgakoudi et al. | |
| 8,496,579 B2 | 7/2013 | Koenig et al. | |
| 8,788,021 B1 | 7/2014 | Flusberg et al. | |
| 8,807,801 B2 | 8/2014 | Oldham et al. | |
| 8,897,858 B2 * | 11/2014 | Sanchez ............... | A61B 5/6848 600/478 |
| 8,912,511 B2 | 12/2014 | Schoenborn et al. | |
| 8,941,087 B2 | 1/2015 | Sun et al. | |
| 9,055,866 B2 | 6/2015 | Narita et al. | |
| 9,411,149 B2 | 8/2016 | Flusberg et al. | |
| 9,433,350 B2 | 9/2016 | Schönborn et al. | |
| 9,433,351 B2 | 9/2016 | Yu et al. | |
| 9,636,020 B2 | 5/2017 | Flusberg et al. | |
| 9,763,577 B2 | 9/2017 | Lee et al. | |
| 9,846,121 B2 | 12/2017 | Schönborn et al. | |
| 9,851,303 B2 | 12/2017 | Huber et al. | |
| 9,983,127 B2 | 5/2018 | Liu et al. | |
| 10,445,879 B1 | 10/2019 | Fuchs et al. | |
| 10,460,150 B2 | 10/2019 | Jackson et al. | |
| 10,499,797 B2 | 12/2019 | Sanchez et al. | |
| 11,172,826 B2 | 11/2021 | Sanchez et al. | |
| 2002/0139920 A1 | 10/2002 | Seibel et al. | |
| 2002/0140942 A1 | 10/2002 | Fee et al. | |
| 2002/0141714 A1 | 10/2002 | Reed et al. | |
| 2002/0146202 A1 | 10/2002 | Reed et al. | |
| 2003/0031410 A1 | 2/2003 | Schnitzer | |
| 2003/0103262 A1 | 6/2003 | Descour et al. | |
| 2003/0117715 A1 | 6/2003 | Schnitzer | |
| 2003/0118305 A1 | 6/2003 | Reed et al. | |
| 2003/0220549 A1 | 11/2003 | Liu et al. | |
| 2003/0236458 A1 * | 12/2003 | Hochman ............. | A61B 5/0059 600/431 |
| 2004/0036838 A1 | 2/2004 | Podoleanu et al. | |
| 2004/0051957 A1 | 3/2004 | Liang | |
| 2004/0064053 A1 * | 4/2004 | Chang ................ | G01N 21/6486 600/478 |
| 2004/0143190 A1 | 7/2004 | Schnitzer | |
| 2004/0249305 A1 | 12/2004 | Reeves et al. | |
| 2004/0254457 A1 | 12/2004 | Van | |
| 2004/0254474 A1 | 12/2004 | Seibel et al. | |
| 2004/0260148 A1 | 12/2004 | Schnitzer | |
| 2005/0157981 A1 | 7/2005 | Berier et al. | |
| 2005/0207668 A1 | 9/2005 | Perchant et al. | |
| 2005/0242298 A1 | 11/2005 | Genet et al. | |
| 2007/0038120 A1 | 2/2007 | Richards-Kortum et al. | |
| 2007/0057211 A1 | 3/2007 | Bahlman et al. | |
| 2007/0159673 A1 | 7/2007 | Freeman et al. | |
| 2007/0167835 A1 | 7/2007 | Yu et al. | |
| 2007/0263226 A1 | 11/2007 | Kurtz et al. | |
| 2007/0283953 A1 | 12/2007 | Angelini et al. | |
| 2007/0290145 A1 | 12/2007 | Viellerobe et al. | |
| 2008/0205833 A1 | 8/2008 | Fu et al. | |
| 2008/0232667 A1 | 9/2008 | Kitamura et al. | |
| 2008/0297922 A1 | 12/2008 | Lule | |
| 2009/0012406 A1 | 1/2009 | Llewellyn et al. | |
| 2009/0015785 A1 | 1/2009 | Blum et al. | |
| 2009/0073455 A1 | 3/2009 | Onimura | |
| 2009/0097108 A1 | 4/2009 | Fox et al. | |
| 2009/0257065 A1 | 10/2009 | Hauger et al. | |
| 2009/0323059 A1 | 12/2009 | Sun et al. | |
| 2010/0110568 A1 | 5/2010 | Margolis | |
| 2010/0177389 A1 | 7/2010 | Rouyer et al. | |
| 2010/0286674 A1 | 11/2010 | Ben-Yakar et al. | |
| 2010/0290042 A1 | 11/2010 | Vakhshoori et al. | |
| 2011/0117025 A1 | 5/2011 | Dacosta et al. | |
| 2011/0125029 A1 | 5/2011 | Wang et al. | |
| 2011/0152744 A1 | 6/2011 | Choi et al. | |
| 2011/0229640 A1 | 9/2011 | Lee et al. | |
| 2011/0229840 A1 | 9/2011 | Liang et al. | |
| 2012/0080616 A1 | 4/2012 | Schoenborn | |
| 2012/0143065 A1 | 6/2012 | Sanchez et al. | |
| 2012/0184827 A1 | 7/2012 | Shwartz et al. | |
| 2012/0261551 A1 | 10/2012 | Rogers | |
| 2012/0281265 A1 | 11/2012 | Zhang et al. | |
| 2013/0063727 A1 | 3/2013 | Xu | |
| 2013/0070249 A1 | 3/2013 | Choi et al. | |
| 2014/0023993 A1 | 1/2014 | Zeng et al. | |
| 2014/0104619 A1 | 4/2014 | Nebosis | |
| 2014/0187879 A1 | 7/2014 | Wood et al. | |
| 2014/0187931 A1 | 7/2014 | Wood et al. | |
| 2014/0187967 A1 | 7/2014 | Wood et al. | |
| 2014/0213897 A1 | 7/2014 | Iftimia et al. | |
| 2014/0276102 A1 | 9/2014 | Lee et al. | |
| 2014/0276103 A1 | 9/2014 | Lee et al. | |
| 2015/0141846 A1 | 5/2015 | Delp et al. | |
| 2015/0157254 A1 | 6/2015 | Sun et al. | |
| 2015/0164327 A1 | 6/2015 | Yaroslavsky et al. | |
| 2015/0238089 A1 | 8/2015 | Fujinuma et al. | |
| 2015/0260978 A1 | 9/2015 | Cremer et al. | |
| 2015/0265155 A1 | 9/2015 | Zalev et al. | |
| 2016/0253466 A1 | 9/2016 | Agaian et al. | |

(56) References Cited

U.S. PATENT DOCUMENTS

| | | |
|---|---|---|
| 2016/0274346 A1 | 9/2016 | Chiang et al. |
| 2016/0317037 A1 | 11/2016 | Lee et al. |
| 2016/0320299 A1 | 11/2016 | Huang et al. |
| 2016/0320837 A1 | 11/2016 | Swedish et al. |
| 2016/0374857 A1 | 12/2016 | Fu et al. |
| 2016/0377546 A1 | 12/2016 | Ragan et al. |
| 2017/0010456 A1 | 1/2017 | Gopinath et al. |
| 2017/0049381 A1 | 2/2017 | Lieber et al. |
| 2017/0143196 A1 | 5/2017 | Liang et al. |
| 2017/0209049 A1 | 7/2017 | Wang et al. |
| 2017/0234675 A1 | 8/2017 | Iddan et al. |
| 2017/0281077 A1 | 10/2017 | Pyun et al. |
| 2017/0284940 A1 | 10/2017 | Butte et al. |
| 2017/0319147 A1 | 11/2017 | Wang et al. |
| 2018/0028079 A1 | 2/2018 | Gurevich et al. |
| 2018/0110971 A1* | 4/2018 | Serrano Carmona ............ A61N 1/36139 |
| 2018/0228552 A1 | 8/2018 | Milner et al. |
| 2019/0129026 A1 | 5/2019 | Sumi et al. |
| 2019/0133452 A1 | 5/2019 | Sanchez et al. |

FOREIGN PATENT DOCUMENTS

| | | |
|---|---|---|
| AU | 2002364332 A1 | 7/2003 |
| AU | 2004297876 A1 | 6/2005 |
| AU | 2007219364 A1 | 4/2008 |
| AU | 2010261751 B2 | 5/2015 |
| AU | 2014236561 B2 | 8/2018 |
| BR | 9911603 A | 2/2001 |
| CA | 2398029 A1 | 8/2001 |
| CA | 2535843 A1 | 6/2005 |
| CA | 2906056 A1 | 9/2014 |
| CA | 2765620 C | 1/2018 |
| CN | 1303539 A | 7/2001 |
| CN | 105473051 A | 4/2016 |
| DE | 19823955 A1 | 12/1999 |
| DE | 102006046925 A1 | 4/2008 |
| EP | 0594388 A1 | 4/1994 |
| EP | 1259163 A2 | 11/2002 |
| EP | 1082816 B1 | 1/2004 |
| EP | 1994874 A1 | 11/2008 |
| EP | 1929939 B1 | 12/2014 |
| EP | 2440119 B1 | 5/2015 |
| EP | 1664854 B1 | 7/2015 |
| EP | 2932892 A1 | 10/2015 |
| EP | 2443503 B1 | 12/2015 |
| EP | 2953215 A1 | 12/2015 |
| EP | 2967280 A2 | 1/2016 |
| EP | 3087423 A1 | 11/2016 |
| EP | 3095001 A2 | 11/2016 |
| EP | 3097443 A1 | 11/2016 |
| EP | 3171766 A1 | 5/2017 |
| EP | 1461601 B1 | 8/2017 |
| EP | 3273285 A1 | 1/2018 |
| JP | 2002517117 A | 6/2002 |
| JP | 2003052642 A | 2/2003 |
| JP | 2003052699 A | 2/2003 |
| JP | 2004500197 A | 1/2004 |
| JP | 2005515434 A | 5/2005 |
| JP | 2006079000 A | 3/2006 |
| JP | 2007503851 A | 3/2007 |
| JP | 2007532982 A | 11/2007 |
| JP | 2008100057 A | 5/2008 |
| JP | 2008539436 A | 11/2008 |
| JP | 2011257215 A | 12/2011 |
| JP | 2016520339 A | 7/2016 |
| JP | 2017502300 A | 1/2017 |
| JP | 2017504836 A | 2/2017 |
| JP | 2017525435 A | 9/2017 |
| KR | 20160037834 A | 4/2016 |
| KR | 20170038024 A | 4/2017 |
| NZ | 520257 A | 10/2005 |
| RU | 2235420 C2 | 8/2004 |
| TW | 201634901 A | 10/2016 |
| TW | 201740101 A | 11/2017 |
| UA | 44939 C2 | 3/2002 |
| WO | WO-9962176 A1 | 12/1999 |
| WO | WO-0159423 A2 | 8/2001 |
| WO | WO-03060493 A1 | 7/2003 |
| WO | WO-2005057244 A2 | 6/2005 |
| WO | WO-2007000165 A1 | 1/2007 |
| WO | WO-2007014213 A2 | 2/2007 |
| WO | WO-2007105495 A1 | 9/2007 |
| WO | WO-2009157229 A1 | 12/2009 |
| WO | WO-2010142672 A1 | 12/2010 |
| WO | WO-2010146134 A2 | 12/2010 |
| WO | WO-2010146134 A3 | 3/2011 |
| WO | WO-2011028595 A2 | 3/2011 |
| WO | WO-2013082156 A1 | 6/2013 |
| WO | WO-2014012110 A2 | 1/2014 |
| WO | WO-2014137357 A1 | 9/2014 |
| WO | WO-2014152389 A1 | 9/2014 |
| WO | WO-2014152797 A2 | 9/2014 |
| WO | WO-2015002614 A1 | 1/2015 |
| WO | WO-2015054666 A1 | 4/2015 |
| WO | WO-2015100421 A1 | 7/2015 |
| WO | WO-2015109323 A2 | 7/2015 |
| WO | WO-2015112770 A1 | 7/2015 |
| WO | WO-2015168594 A1 | 11/2015 |
| WO | WO-2015185620 A1 | 12/2015 |
| WO | WO-2016015052 A1 | 1/2016 |
| WO | WO-2016145633 A1 | 9/2016 |
| WO | WO-2017139716 A1 | 8/2017 |
| WO | WO-2017156182 A1 | 9/2017 |
| WO | WO-2017173315 A1 | 10/2017 |
| WO | WO-2018018160 A1 | 2/2018 |
| WO | WO-2018201082 A1 | 11/2018 |
| WO | WO-2020102442 A1 | 5/2020 |
| WO | WO-2021097142 A1 | 5/2021 |

OTHER PUBLICATIONS

EP12853081.3 Examination Report dated Nov. 9, 2017.
PCT/US2019/061306 International Search Report dated Mar. 9, 2020.
Co-pending U.S. Appl. No. 17/096,602, inventors Sanchez; Gabriel et al., filed Nov. 12, 2020.
EP18791038.5 The Extended European Search Report dated Dec. 22, 2020.
U.S. Appl. No. 16/123,447 Office Action dated Dec. 10, 2020.
Co-pending U.S. Application No. 202117495717, inventors Sanchez; Gabriel et al., filed on Oct. 6, 2021.
U.S. Appl. No. 16/585,789 Office Action dated Feb. 23, 2022.
Anderson, et al., Contributions of muscle forces and tow-off kinematics to peak knee flexion during the swing phase of normal gait: an induced position analysis, Journal of Biomechanics, 37:731-737 (2004).
Armstrong, et al., In vivo size and shape measurement of the human upper airway using endoscopic long range optical coherence tomography, Opt. Express, 11:1817-26 (2003).
Botcherby, et al. Fast measurement of sarcomere length and cell orientation in Langendorff-perfused hearts using remote focusing microscopy. Circ Res. Sep. 13, 2013;113(7):863-70. doi: 10.1161/CIRCRESAHA.113.301704. Epub Jul. 30, 2013.
Boulesteix, et al., Second-harmonic Microscopy of Unstained Living Cardiac Myocytes: Measurements of sarcomere length with 20-nm accuracy, Optics Letters, Sep. 1, 2004, 29(17):2031-33.
Brown, et al., Dynamic imaging of collagen and its modulation in tumors in vivo using second-harmonic generation, Nature Medicine, 9:796-800 (2003).
Campagnola, et al. Three-dimensional high-resolution second-harmonic generation imaging of endogenous structural proteins in biological tissues. Biophysical Journal. 2002; 81:493-508.
Campagnola, et al., Nonlinear Optical Spectroscopy, Optics & Photonics News, Jun. 2003, pp. 40-45.
Chu, et al., Studies of X(2)/X(3) Tensors in Submicron-Scaled Bio-Tissues by Polarization Harmonics Optical Microscopy, Biophysical Journal, 86: 3914-22 (Jun. 2004).
Co-pending U.S. Appl. No. 16/585,789, filed Sep. 27, 2019.

(56) References Cited

OTHER PUBLICATIONS

Delp, et al., An Interactive Graphics-based Model of the Lower Extremity to Study Orthopedic Surgical Procedures, IEEE Trans Biomed Eng., 37: 757-767. (1990).
Delp, et al., Open Sim: Open-Source Software to create and analyze dynamic simulations of movement, Biomedical Engineering IEEE, 54: 1940-50 (Nov. 2007) Abstract Only.
Dutton, H. Understanding Optical Communications, IBM, International Technical Support Organization Sep. 1998. Available at http://www.redbooks.ibm.com.
Edman, et al., Depression of tetanic force induced by loaded shortening of frog muscle fibres, J Physiol., 466: 535-552 (1993).
EP17764041.4 The Extended European Search Report dated Sep. 25, 2019.
EPO. European Patent Application No. 12853081, Supplementary European Search Report. (dated Jun. 22, 2015).
EPO. European Patent Application No. 12853081.3, Examination Report, 6 pgs. (dated Nov. 24, 2016).
Flusberg, et al., In Vivo Brain Imaging Using a Portable 3.9 Gram Two-photon Fluorescence Microendoscope, Optics Letters 30(17):2272-74 (Sep. 2005).
Freund, et al., Connective Tissue Polarity: Optical Second-harmonic Microscopy, Crossed-beam Summation, and Small-angle Scattering in Rat-tail Tendon, Biophysical Journal, 50: 693-712 (Oct. 1986).
Friden, et al., Physiologic consequences of surgical lengthening of extensor carpi radialis brevis muscle-tendon junction for tennis elbow, J Hand Surg., 19: 269-274 (1994). Abstract Only.
Fu, et al., Integration of a Double-clad Photonic Crystal Fiber, a GRIN lens and a MEMS mirror for nonlinear optical endoscopy, BIO Meeting, Fort Lauderdale (Mar. 19, 2006).
Fu, et al., Nonlinear optical endoscopy based on a double clad photonic crystal fiber and a MEMS mirror, Optics Express, 14(3):1027-32 (Feb. 2006).
Gobel, et al. New angles on neuronal dendrites in vivo. J Neurophysiol. Dec. 2007;98(6):3770-9. Epub Sep. 26, 2007.
Gollapudi, et al., Experimental determination of sarcomere force-length relationship in type-1 human skeletal muscle fibers, J Biomech 42, pp. 2011-2016 (2009) Abstract Only.
Gordon, et al., The variation in isometric tension with sarcomere length in vertebrate muscle fibers, J Physiol,184: 170-92. (1966).
Guo, et al., Second-harmonic Tomography of Tissues, Optics Letters, Sep. 1, 1997, 22(17):1323-25.
Guo, et al., Subsurface tumor progression investigated by noninvasive optical second harmonic tomography, Proc. Nat'l. Academy of Science, Sep. 1999, 96: 10854-856.
Helmchen, et al., Deep Tissue two-photon microscopy, Nature Methods, 2(12):932-940 (Dec. 2005).
Imaging and Optical technology at Aberdeen, Optics and Laser Technology 25(6), pp. 399-405 (1993).
Infantolino, et al., Individual sarcomere lengths in whole muscle fibers and optimal fiber length computation, Analrec (Hoboken) 293, pp. 1913-1919 (2010).
International search report and written opinion dated Jul. 26, 2017 for PCT Application No. US-201721439.
Julian, et al., Intersarcomere dynamics during fixed-end tetanic contractions of frog muscle fibres, J Physiol., 293: 365-78 (1979).
Julian, et al., Sarcomere length-tension relations of frog skinned muscle fibres at lengths above the optimum, J Physiol., 304: 529-39 (1980).
Jung, et al. Miniaturized probe using 2 axis MEMS scanner for endoscopic multiphoton excitation microscopy. Proceedings of SPIE—The International Society for Optical Engineering, vol. 6851, Mar. 2008, pp. 1-7.
Jung, et al., In vivo mammalian brain imaging using one- and two-photon fluorescence microendoscopy, J. Neurophysiol, 92:3121-33 (May 2004).
Jung, et al., Multiphoton endoscopy, Optics Letters, 28(11):902-904 (Jun. 2003).

Koch, G. MEMS-based scanning device facilitates microendoscopy. Optics Letters, Jul. 1, 2006. pp. 1-3, Online: http://www.photonics.com/Article.aspx?AID=43392, Accessed Feb. 20, 2016.
Konig, et al., High-resolution multiphoton tomography of human skin with subcellular spatial resolution and picosecond lime resolution, Society of Photo-Optical Instrum Engineers. (2003) Abstract Only.
Lee, et al., Integrated semiconductor optical sensor for chronic, minimally-invasive imaging of brain functions, Proceedings of the 28th IEEE, pp. 1025-1028 (Aug.-Sep. 2006).
Levene, et al., In vivo multiphoton microscopy of deep brain tissue, J. Neurophysiol, 91: 1908-12 (Dec. 2003).
Lieber, et al., Biomechanical properties of the brachioradialis muscle: Implications for surgical tendon transfer, The Journal of Hand Surgery, 30A(2):273-282 (Mar. 2005).
Lieber, et al., In Vivo Measurement of Human Wrist Extensor Muscle Sarcomere Length Changes, Journal of Neurophysiology, 71(3): 874-881 (Mar. 1994).
Lieber, et al., Sarcomere length in wrist extensor muscles, Changes may provide insights into the etiology of chronic lateral epicondylitis, Acta Orthop Scand, 68:249-254 (1997).
Ljung, et al., Sarcomere length varies with wrist ulnar deviation but not forearm pronation in the extensor carpi radialis brevis muscle, J Biomech., 32:199-202 (1999).
Llewellyn, et al., Minimally invasive high-speed imaging of sarcomere contractile dynamics in mice and humans, Nature 454, 784-788 (2008).
Manal, et al. A real-time EMG-driven virtual arm, Comput. Bioi. Med., 32(1):25-26 (Jan. 2002) Abstract Only.
Mertz, et al., Second-harmonic generation by focused excitation of inhomogeneously distributed scatterers, Optics Communications 196: 325-330 (2001).
Mertz, Nonlinear microscopy: New techniques and applications, Current Opinion in Neurobiology, 14:610-616 (2004).
Messerschmidt, et al., Novel concept of GRIN optical systems for high resolution microendoscopy. Part 1: Physical aspects, Proc. of SPIE 6432, pp. 643202-1-643202-9 (2007).
Mohler, et al., Second-harmonic generation imaging of endogenous structural proteins, Methods, 29:97-109 (2003).
Monfared, et al., In Vivo Imaging of Mammalian Cochlear Blood Flow Using Fluorescence Microendoscope, Otology and Neurotology, 27:144-152 (2006).
Moreaux, et al., Coherent Scattering in Multi-Harmonic Light Microscopy, Biophysical Journal, 80: 1568-74 (Mar. 2001).
Murray, et al., Variability in surgical technique for brachioradialis tendon transfer, Evidence and implications, J Bone Joint Surg. Am., 88: 2009-16 (2006).
Niell, et al., Live Optical Imaging of Nervous System Development, Annu. Rev. Physiol., 66:771-798 and C1-C5 (2004).
Nucciotti, et al., Functional imaging of muscle cells by Second Harmonic Generation, Proc. of SPIE, 6089: 608911-1-608911-8 (2006).
Office action dated Jan. 27, 2017 for U.S. Appl. No. 14/546,085.
Office Action dated Nov. 3, 2017 for U.S. Appl. No. 14/546,085.
Olivier, et al. Cell lineage reconstruction of early zebrafish embryos using label-free nonlinear microscopy. Science. Aug. 20, 2010;329(5994):967-71. doi: 10.1126/science.1189428.
Panchangam, et al., A novel optical imaging system for investigating sarcomere dynamics in single skeletal muscle fibers, Proc. of SPIE, 6088: 608808-1-608808-11 (2006).
PCT/US12/66860 International Search Report and Written Opinion dated Apr. 17, 2013.
PCT/US2018/030011 International Search Report and Written Opinion dated Aug. 14, 2018.
Plotnikov, et al., Characterization of the Myosin-based source for Second-Harmonic Generation from muscle sarcomeres, Biophysical Journal, 90:693-703 (Jan. 2006).
Plotnikov, et al., Measurement of muscle disease by quantitative second-harmonic generation imaging, J. Biomed. Opt. 13 (Aug. 2008) Abstract Only.
Plotnikov, et al., Optical Clearing for Improved Contrast in Second Harmonic Generation Imaging of Skeletal Muscle, Biophysical Journal, 90:328-339 (Jan. 2006).

(56) References Cited

OTHER PUBLICATIONS

Ponten, et al., Intraoperative muscle measurements reveal a relationship between contracture formation and muscle remodeling, Muscle & Nerve 36, pp. 47-54 (Jul. 2007).
Rothstein, et al., Multi-photon excitation microscopy in intact animals, Journal of Microscopy, 22:58-64 (2006).
Rothstein, et al., Skeletal Muscle NAD(P)H Two-photon fluorescence microscopy in vivo: Topology and Optical inner filters, Biophysical Journal, 88: 2165-76 (Mar. 2005).
Schenkl, et al., Applications of rigid and flexible GRIN-endoscopes, Proc. of SPIE 6433, pp. 64330N-1- 64330N-7 (2007).
Shaw, et al., Infrared spectroscopy of dystrophic mdx mouse muscle tissue distinguishes among treatment groups, J. Applied Physiol. 81: 2328-2335 (1996).
Smith, et al., Hamstring contractures in children with spastic cerebral palsy result from a stiffer extracellular matrix and increased in vivo sarcomere length, J Physiol., 589: 2625-2639. (2011).
U.S. Appl. No. 14/546,085 Notice of Allowance dated Jul. 22, 2019.
U.S. Appl. No. 14/546,085 Office Action dated Feb. 26, 2016.
U.S. Appl. No. 14/546,085 Office Action dated Jun. 8, 2016.
U.S. Appl. No. 14/546,085 Office Action dated Oct. 10, 2018.
Williams, et al., Interpreting Second-Harmonic Generation Images of Collagen I Fibrils, Biophysical Journal, 88:1377-86 (Feb. 2005).
Zipfel, et al., Live tissue intrinsic emission microscopy using multiphoton-excited native fluorescence and second harmonic generation, PNAS 100(12):7075-80 (Jun. 2003).
Zoumi, et al., Imaging cells and Extracellular Matrix in vivo by using Second-harmonic Generation and two-photon excited fluorescence, PNAS, Aug. 20, 2002, 99(17):11014-19.
Co-pending U.S. Application No. 202117317661, inventors Sanchez; Gabriel et al., filed on May 11, 2021.
EP 20199801.0European Search Report, dated Jun. 11, 2021, 8 pages.
U.S. Appl. No. 16/123,447 Notice of Allowance dated Aug. 11, 2021.
EP19885962.1 Extended European Search Report dated Jun. 20, 2022.
U.S. Appl. No. 16/585,789 Final Office Action dated Oct. 14, 2022.
U.S. Appl. No. 17/096,602 Office Action dated Nov. 7, 2022.
U.S. Appl. No. 17/495,717 Office Action dated Nov. 8, 2022.

\* cited by examiner

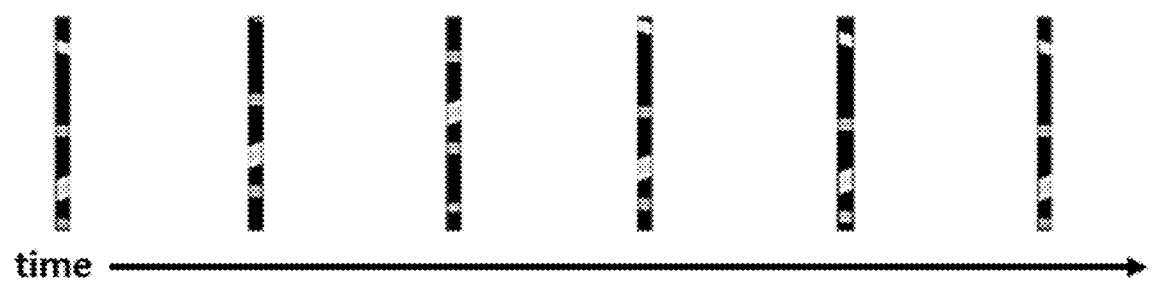
*FIG. 11C*
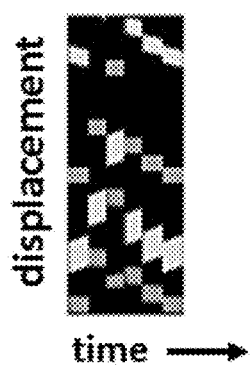 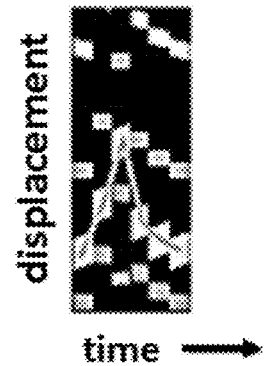 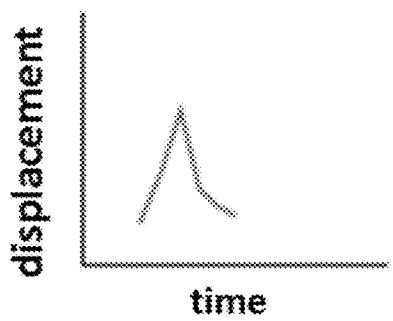
*FIG. 11D*   *FIG. 11E*   *FIG. 11F*

SYSTEMS AND METHODS FOR IMAGING AND MEASUREMENT OF SARCOMERES

CROSS-REFERENCE

This application is a continuation of International Application No. PCT/US2018/030011, filed Apr. 27, 2018, which claims the benefit of U.S. Provisional Patent Application No. 62/491,868, filed Apr. 28, 2017, which are entirely incorporated herein by reference.

BACKGROUND

Generalized decline in muscle mass and strength is prevalent within aging populations. Sarcopenia is an age related decline in muscle mass, first characterized by muscle atrophy, and is one of the most common causes of functional decline and loss of independence in older adults. Those suffering from sarcopenia have larger instances of falls, disability, and frailty. Sarcopenia is also associated with acute and chronic disease states, increased insulin resistance, fatigue, and morality.

Modern approaches to diagnosing and studying sarcopenia and other muscular degenerative diseases are primarily based on physical performance measures. Assessment of muscle mass and strength may be a secondary diagnostic step due to cost and complexity. Techniques for assessing muscle mass may range in complexity from atomic detection to anatomic measurements. Some techniques, such as magnetic resonance imaging (MRI) and computed tomography (CT) offer high validity at the expense of complexity and cost. The preferred clinical method for assessing muscle mass, bioelectrical impedance analysis, offers low cost diagnostics and ease of use at the expense of validity and reproducibility.

SUMMARY

Provided herein are methods and apparatuses that may be useful for imaging and measurement of tissue, such as muscle tissue. This may be used to measure various type of muscle tissue, including sarcomeres.

In an aspect, an apparatus for identifying and/or analyzing muscle tissue of a subject comprises a light source for generating a beam of light, a first probe and a second probe separate from the first probe, where the first probe transmits the beam of light from the light source to a muscle tissue of the subject, where upon contacting the muscle tissue, the beam of light generates at least one signal intrinsic to a property of the muscle tissue, and where the second probe collects the at least one signal intrinsic to the property of the muscle tissue; a collection unit in optical communication with the second probe, where the collection unit collects the at least one signal intrinsic to the property of the muscle tissue; and a computer controller operatively coupled to the light source and the collection unit, where the computer controller is programmed to (i) direct the light source to generate the beam of light, and (ii) process the at least one signal intrinsic to the property of the muscle tissue collected by the collection unit to generate at least one image of the muscle tissue, where the at least one image is usable to identify the muscle tissue of the subject.

In some embodiments, the apparatus is portable. In some embodiments, the apparatus has a weight of at most about 5 pounds. In some embodiments, the at least one signal includes a plurality of signals. In some embodiments, the at least one signal is an optical signal. In some embodiments, the first probe and the second probe comprise needles. In some embodiments, the muscle tissue is disposed between the first probe and the second probe. In some embodiments, the first probe and the second probe are separated by a distance of about 1 millimeter or less.

In some embodiments, the beam of light comprises unpolarized light. In some embodiments, the beam of light comprises polarized light. In some embodiments, the apparatus further comprising a telecentric objective in optical communication with the first probe. In some embodiments, the apparatus further comprises a dichroic mirror in optical communication with the first probe and the second probe, wherein the dichroic mirror separates the beam of light from the at least one signal intrinsic to the property of the muscle tissue. In some embodiments, a wavelength of the beam of light is greater than about 400 nm. In some embodiments, the at least one signal intrinsic to the property of the muscle tissue is detected by a photomultiplier tube sensor. In some embodiments, a power and a gain of the photomultiplier tube sensor are modulated to enhance a quality of the at least one image. In some embodiments, the at least one image is usable to identify a muscle disease in the muscle tissue. In some embodiments, the muscle disease is sarcopenia. In some embodiments, the muscle disease is a muscular degenerative disease.

In some embodiments, the at least one signal intrinsic to the property of the muscle tissue is a forward second harmonic generation signal. In some embodiments, the at least one signal intrinsic to the property of the muscle tissue is an autofluorescence signal. In some embodiments, the at least one signal intrinsic to the property of the muscle tissue is a forward second harmonic generation signal, autofluorescence signal, or combination thereof. In some embodiments, the at least one image is usable to measure sarcomere length.

In an aspect, an apparatus for identifying and/or analyzing muscle tissue of a subject comprises a light source for generating a beam of light; an optical element comprising a probe that transmits the beam of light from the light source to a muscle tissue of a subject, where upon contacting the muscle tissue the beam of light generates at least one signal intrinsic to a property of the muscle tissue; a stimulation unit comprising at least one electrode in electrical communication with the probe such that a circuit is formed between the at least one electrode and the probe during stimulation, and wherein the stimulation unit locally stimulates the muscle tissue while the beam of light is transmitted to the muscle tissue; a collection unit that collects the at least one signal intrinsic to the property of the muscle tissue; and a computer controller operatively coupled to the light source, the stimulation device, and the collection unit, where the computer controller is programmed to (i) direct the light source to generate the beam of light, (ii) direct the stimulation device to stimulate the muscle tissue while the beam of light is transmitted to the muscle tissue, and (iii) process the at least one signal intrinsic to the property of the muscle tissue collected by the collection unit to generate at least one image of the muscle tissue, where the at least one image is usable to identify the muscle tissue of the subject.

In some embodiments, the apparatus is portable. In some embodiments, the apparatus has a weight of at most about 5 pounds. In some embodiments, the at least one signal includes a plurality of signals. In some embodiments, the at least one signal is an optical signal. In some embodiments, the probe comprises a first probe and a second probe. In some embodiments, the first probe and the second probe comprise needles. In some embodiments, the muscle tissue is disposed between the first probe and the second probe. In some embodiments, the first probe and the second probe are separated by a distance of about 1 millimeter or less. In some embodiments, one of the first probe and the second probe is used to stimulate the muscle tissue and another of the first probe and the second probe is used to measure biologic electrical signals.

In some embodiments, the beam of light comprises unpolarized light. In some embodiments, the beam of light comprises polarized light. In some embodiments, the optical element further comprises a telecentric objective. In some embodiments, the optical element further comprises a dichroic mirror and wherein the dichroic mirror separates the beam of light from the at least one signal intrinsic to the property of the muscle tissue. In some embodiments, a wavelength of the beam of light is greater than about 400 nm.

In some embodiments, the stimulation device comprises at least one anode. In some embodiments, the optical element acts as a cathode. In some embodiments, the at least one anode is four anodes. In some embodiments, the four anodes are stimulated individually. In some embodiments, the four anodes are stimulated simultaneously.

In some embodiments, the at least one signal intrinsic to the property of the muscle tissue is detected by a photomultiplier tube sensor. In some embodiments, a power and a gain of the photomultiplier tube sensor are modulated to enhance a quality of the at least one image. In some embodiments, the at least one image is usable to identify a muscle disease in the muscle tissue. In some embodiments, the muscle disease is sarcopenia. In some embodiments, the muscle disease is a muscular degenerative disease.

In some embodiments, the at least one signal intrinsic to the property of the muscle tissue is a forward second harmonic generation signal. In some embodiments, the at least one signal intrinsic to the property of the muscle tissue is an autofluorescence signal. In some embodiments, the at least one signal intrinsic to the property of the muscle tissue is a forward second harmonic generation signal, autofluorescence signal, or combination thereof. In some embodiments, the at least one image is used to measure sarcomere length. In some embodiments, the at least one image is used to measure sarcomere displacement during stimulation.

In an aspect, a method for identifying and/or analyzing muscle tissue of a subject comprises inserting at least a portion of a probe set into the muscle tissue of a subject, where the probe set comprises a first probe and a second probe; transmitting a beam of light from a light source to the muscle tissue via the first probe, where upon contacting the muscle tissue, the beam of light generates at least one signal intrinsic to a property of the muscle tissue; using the second probe to direct the at least one signal intrinsic to the property of the muscle tissue to a collection unit; and using a computer controller to process the at least one signal intrinsic to the property of the muscle tissue collected by the collection unit to generate at least one image of the muscle tissue, where the at least one image is usable to identify the muscle tissue of the subject.

In some embodiments, the at least one signal includes a plurality of signals. In some embodiments, the at least one signal is an optical signal. In some embodiments, the first probe and the second probe comprise needles. In some embodiments, the muscle tissue is disposed between the first probe and the second probe. In some embodiments, the first probe and the second probe are separated by a distance of about 1 millimeter or less.

In some embodiments, the beam of light is a pulsed beam of light. In some embodiments, the beam of light comprises unpolarized light. In some embodiments, the beam of light comprises polarized light. In some embodiments, the optical element further comprises a telecentric objective. In some embodiments, the optical element further comprises a dichroic mirror and wherein the dichroic mirror separates the beam of light from the at least one signal intrinsic to the property of the muscle tissue. In some embodiments, a wavelength of the beam of light is greater than about 400 nm.

In some embodiments, the at least one signal intrinsic to the property of the muscle tissue is detected by a photomultiplier tube sensor. In some embodiments, a power and a gain of the photomultiplier tube sensor are modulated to enhance a quality of the at least one image. In some embodiments, the at least one image is usable to identify a muscle disease in the muscle tissue. In some embodiments, the muscle disease is sarcopenia. In some embodiments, the muscle disease is a muscular degenerative disease.

In some embodiments, the at least one signal intrinsic to the property of the muscle tissue is a forward second harmonic generation signal. In some embodiments, the at least one signal intrinsic to the property of the muscle tissue is an autofluorescence signal. In some embodiments, the at least one signal intrinsic to the property of the muscle tissue is a forward second harmonic generation signal, an autofluorescence signal, or combination thereof. In some embodiments, the at least one image is usable to measure sarcomere length. In some embodiments, the at least one image is part of a video generated by the computer.

In an aspect, a method for identifying and/or analyzing a muscle tissue of a subject comprises inserting at least a portion of an optical element into a muscle tissue of a subject, where the at least the portion of the optical element comprises a probe; transmitting a beam of light from a light source to the muscle tissue via the probe, where upon contacting the muscle tissue, the beam of light generates at least one signal intrinsic to a property of the muscle tissue; stimulating the muscle tissue with a stimulation unit, wherein the stimulation unit comprises at least one electrode in electrical communication with the probe such that circuit is formed between the at least one electrode and the probe; using the probe to direct he at least one signal intrinsic to the property of the muscle tissue to a collection unit; and using a computer to process the at least one signal intrinsic to the property of the muscle tissue collected by the collection unit to generate at least one image of the muscle tissue during stimulation of the muscle tissue, where the at least one image is usable to identify the muscle tissue of the subject.

In some embodiments, the at least one signal includes a plurality of signals. In some embodiments, the at least one signal is an optical signal. In some embodiments, the probe comprises a first probe and a second probe. In some embodiments, the first probe and the second probe comprise needles. In some embodiments, the muscle tissue is disposed between the first probe and the second probe. In some embodiments, the first probe and the second probe are separated by a distance of about 1 millimeter or less. In some embodiments, one of the first probe and the second probe is used to stimulate the muscle tissue and another of the first probe and the second probe is used to measure biologic electrical signals.

In some embodiments, the beam of light is a pulsed beam of light. In some embodiments, the beam of light comprises unpolarized light. In some embodiments, the beam of light comprises polarized light. In some embodiments, the optical element further comprises a telecentric objective. In some embodiments, the optical element further comprises a dichroic mirror and wherein the dichroic mirror separates the beam of light from the at least one signal intrinsic to the property of the muscle tissue. In some embodiments, a wavelength of the beam of light is greater than about 400 nm.

In some embodiments, the stimulation device comprises at least one anode. In some embodiments, the optical element acts as a cathode during stimulation. In some embodiments, the at least one electrode is four anodes. In some embodiments, the four anodes are stimulated individually. In some embodiments, the four anodes are stimulated simultaneously.

In some embodiments, the at least one signal intrinsic to the property of the muscle tissue is detected by a photomultiplier tube sensor. In some embodiments, a power and a gain of the photomultiplier tube sensor are modulated to enhance a quality of the at least one image. In some embodiments, the at least one image is usable to identify a muscle disease in the muscle tissue. In some embodiments, the muscle disease is sarcopenia. In some embodiments, the muscle disease is a muscular degenerative disease.

In some embodiments, the at least one signal intrinsic to the property of the muscle tissue is a forward second harmonic generation signal. In some embodiments, the at least one signal intrinsic to the property of the muscle tissue is an autofluorescence signal. In some embodiments, the at least on signal intrinsic to the property of the muscle tissue is a forward second harmonic generation signal, an autofluorescence signal, or combination thereof. In some embodiments, the at least one image is used to measure sarcomere length. In some embodiments, the at least one image is used to measure sarcomere displacement during stimulation. In some embodiments, the at least one image is part of a video generated by the computer.

In another aspect, the present disclosure provides a method for identifying or analyzing a muscle tissue of a subject, comprising using a first probe of a probe set to direct a beam of light to the muscle tissue, using a second probe of the probe set to collect at least on signal from within the muscle tissue, which second probe is different than the first probe, wherein the at least one signal is generated in response to directing the beam of light to the muscle tissue, and processing the at least one signal to identify a health state or physiological condition of the muscle tissue. In some embodiments, at least a portion of the probe set is within the muscle tissue.

In another aspect, the present disclosure provides a method for identifying and/or analyzing a muscle tissue of a subject in real-time, comprising subjecting the muscle tissue to directional stimulation, collecting signals from within the muscle tissue at multiple time points in real-time during or subsequent to subjecting the muscle tissue to directional stimulation, and using the signals to identify a health state or physiological condition of the muscle tissue. In some embodiments, the stimulation causes the muscle tissue to undergo contraction and relaxation.

In another aspect, the present disclosure provides a method for identifying or analyzing a muscle tissue of a subject, comprising directing a beam of light to a tissue of the subject, which tissue comprises the muscle tissue and non-muscle tissue, collecting at least one signal from within the tissue, which at least one signal is generated in response to directing the beam of light to the muscle tissue, and generating an image that selectively identifies the muscle tissue from the non-muscle tissue. In some embodiments, the image identifies the muscle tissue at a first intensity and the non-muscle tissue at a second intensity, which first intensity is greater than the second intensity. In some embodiments, the at least one signal comprises a forward second harmonic generation signal. In some embodiments, the beam of light is directed to the tissue at a first location and the at least one signal is collected from within the tissue at a second location, which first location is different than the second location.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 1A is an example schematic of the optical components of the optical element;

FIG. 1B is an example image of sarcomeres generated from second harmonic generation signals;

FIG. 1C is an example image of sarcomeres during dynamic imaging;

FIG. 2A is an illustration of the imaging system and use of the imaging system on a subject; FIG. 2B is a diagram of sarcomere viewing angle;

FIG. 6A shows skin marking and electrode placement; FIG. 6B shows the insertion of the optical element probes by rapid injection; FIG. 6C shows the optical element and electrode pad position on a subject; FIG. 6D shows microscope placement;

FIG. 8A shows a representative static image of muscle tissue of a subjects and the measured average sarcomere length of the subjects; FIG. 8B shows a representative static image of a collagen bundle superimposed on sarcomere bands and the measured average percent of structured collagen of different aged subjects; FIG. 8C shows a representative static image of unstructured collagen and average percent of unstructured collagen of different aged subjects;

FIG. 9A shows hypothetical data of motor unit as a function of electrical stimulation voltage for a subject; FIG. 9B shows hypothetical data of the average number of motor units recruited for different aged subjects; FIG. 9C shows hypothetical data of differences in initiation and jump voltages for different aged subjects;

FIG. 10A shows rise time distribution for different aged subjects; FIG. 10B shows half relaxation time dynamic of motor units for different aged subjects;

FIGS. 11A-11F show example schematics of measuring contractility using a line scan; FIG. 11A shows a panel of two-dimensional structure movement over time during electrical stimulation; FIG. 11B shows an example of a line scan field of view; FIG. 11C shows an example line scan across the field of view; FIG. 11D shows an assembled image of progressive line scans; FIG. 11E shows a curve fit to the assembled line scan image; FIG. 11F shows an extracted plot of displacement as a function of time;

FIG. 13A shows a representative trace taken during stimulation with a distal lateral anode; FIG. 13B shows a representative trace taken during stimulation with a proximal lateral anode; FIG. 13C shows a representative trace taken during stimulation with a distal medial anode; FIG. 13D shows a representative trace taken during stimulation with a proximal medial anode;

FIG. 15A shows the tissue displacement as a function of stimulation voltages that recruit additional motor units for young subjects; FIG. 15B shows the average initiation voltage for young, elderly, male, and female subjects; FIG. 15C shows the average jump voltage for young, elderly, male, and female subjects;

FIG. 16A shows the average contraction time for a first and second step for different aged subjects; FIG. 16B shows the average relaxation half times for a first and second step for different aged subjects;

FIG. 18A shows a representative image of bundled collagen; FIG. 18B shows a representative image of unstructured collagen; FIG. 18C shows the trend of initiation voltage as a function of proportion of unstructured collagen; FIG. 18D shows the average portions of frames with visible tissue for different aged subjects;

FIG. 19A shows knee extension torque as a function of contractility for different aged subjects; FIG. 19B shows grip strength as a function of contractility for different aged subjects; FIG. 19C shows walking speed as a function of contractility for different aged subjects;

DETAILED DESCRIPTION

Figure 1A:
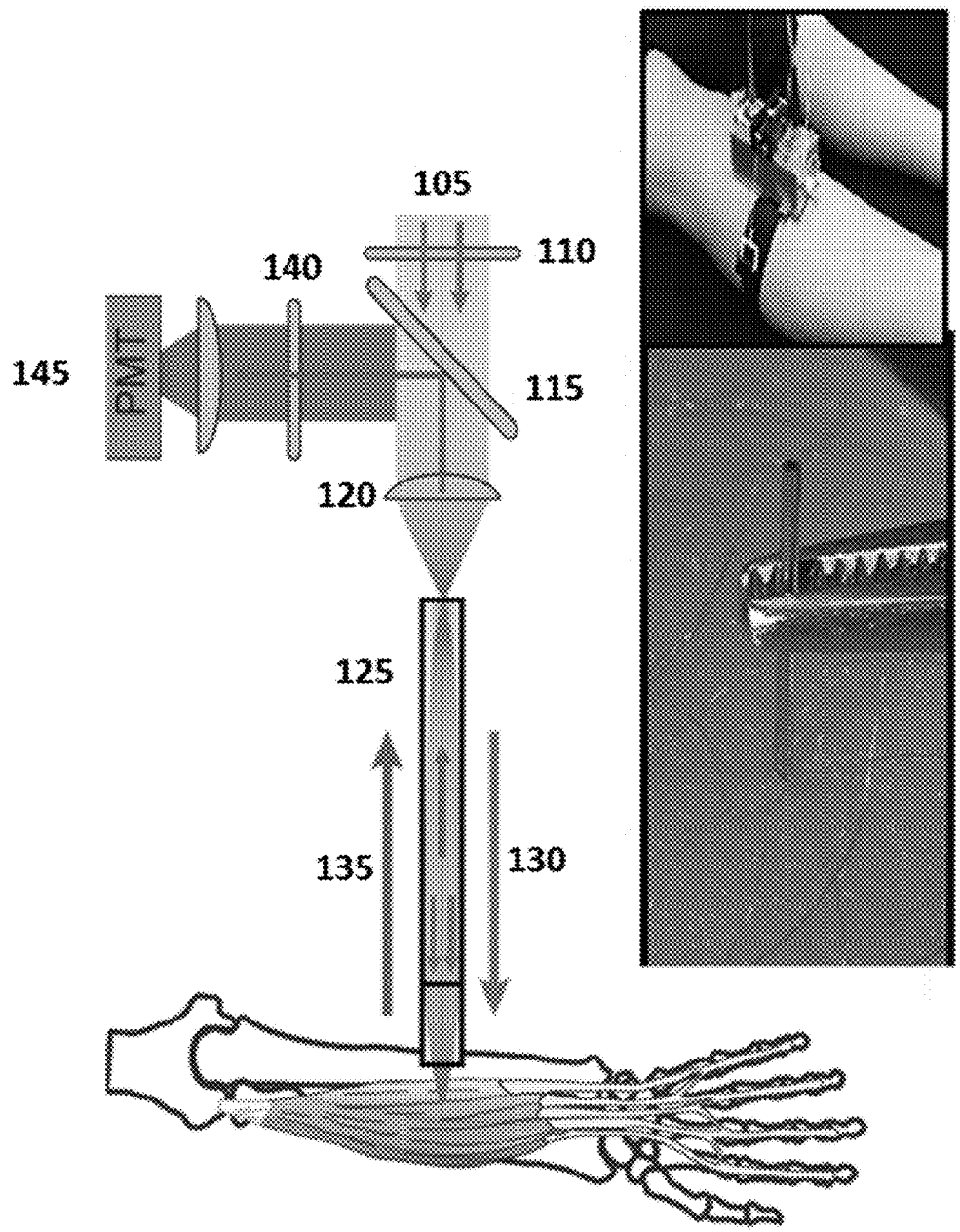
FIGS. 1A-1C show an overview of the optical element and example images generated from the element.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "subject," as used herein, generally refers to an animal, such as a mammal. A subject may be a human or non-human mammal. A subject may be afflicted with a disease or suspected of being afflicted with a disease. In some cases, the subject may be treated to alleviate the symptoms of the disease or cure the subject of the disease. A subject may be a patient undergoing treatment by a healthcare provider, such as a doctor.

The term "disease," as used herein, generally refers to an abnormal condition, or a disorder of a biological function or a biological structure such as an organ, that affects part or all of a subject. A disease may be caused by factors originally from an external source, such as infectious disease, or it may be caused by internal dysfunctions, such as autoimmune diseases. A disease can refer to any condition that causes pain, dysfunction, distress, social problems, and/or death to the subject afflicted. A disease may be an acute condition or a chronic condition. A disease may refer to an infectious disease, which may result from the presence of pathogenic microbial agents, including viruses, bacteria, fungi, protozoa, multicellular organisms, and aberrant proteins (e.g., prions). A disease may refer to a non-infectious disease, including but not limited to cancer and genetic diseases. In some cases, a disease can be cured. In some cases, a disease cannot be cured.

The term "muscle tissue," as used herein, generally refers to striated, smooth, or cardiac muscle tissue. Striated muscle tissue, or rough muscle tissue, may include muscle fibers which contain myofibrils. Myofibrils may be composed of repeating units of sarcomeres. Smooth muscle, or non-striated muscle, may include single-unit and multiunit muscle composed of myocytes. Cardiac muscle may contain myofibrils comprising repeating units of sarcomeres. Muscle tissue may also comprise an endomysium which may act as a connective tissue that sheaths the individual muscle fibers or muscle cells. The endomysium may be composed primarily of collagen.

The term "motor unit," as used herein, generally refers a tissue made up of a motor neuron and skeletal muscle fibers. Groups of motor units may work together to coordinate the contractions of a single muscle. Activating a motor unit may cause the motor unit fibers to contract.

The terms "motor unit recruitment" or "recruitment," as used herein, generally refers to the activation of additional motor units to increase the contractile strength of a muscle. Generally, the smallest motor units will contract first, followed by motor units increasing in size based on the size of the load.

The term "light," as used herein, generally refers to electromagnetic radiation in a range of wavelengths from infrared (e.g., about 700 nm to about 1 mm) through the ultraviolet (e.g., about 10 nm to about 380 nm).

The term "ambient light," as used herein, generally refers to the light surrounding an environment or subject, such as the light in a medical examination or operating room.

The term "focal plane," as used herein, generally refers a plane that is perpendicular to the axis of a lens or mirror and passes through the focal point of the lens or mirror. A focal point generally refers to a point on the axis of a lens or mirror to which parallel rays of light can converge to form an image of a sample.

The term "fluorescence," as used herein, generally refers to radiation that can be emitted as the result of the absorption of incident electromagnetic radiation of one or more different wavelengths. In some cases, fluorescence may result from emissions from exogenously provided tags and/or markers. In some cases, fluorescence may result as an inherent response of one or more endogenous molecules to excitation with electromagnetic radiation.

The term "autofluorescence," as used herein, generally refers to fluorescence from one or more endogenous molecules to excitation with electromagnetic radiation.

The term "multi-photon excitation," as used herein, generally refers to excitation of a fluorophore by more than one photon, resulting in the emission of a fluorescence photon. In some cases, the emitted photon is at a higher energy than the excitatory photons.

The terms "second harmonic generation" and "SHG," as used herein, generally refer to a nonlinear optical process in which photons interacting with a nonlinear material are effectively "combined" to form new photons with about twice the energy, and therefore about twice the frequency and about half ($\frac{1}{2}$) the wavelength of the initial photons.

The terms "backward second harmonic generation" and "BSHG," as used herein, generally refer to second harmonic generation signals that emit backward from a sample. For example, incident light may contact a tissue and a subset of that incident light may be directed back towards the light source as a BSHG signal. BSHG signals may not phase match and, therefore, the BSHG signals may constructively or destructively interfere and alter the signal strength.

The terms "forward second harmonic generation" and "FSHG" may be used interchangeably and, as used herein, generally refer to second harmonic generation signals that emit forward form a sample. For example, incident light may contact a tissue and a subset of that incident lay may be directed forward through the tissue as a FSHG signal. FSHG signals may phase match and, therefore, FSHG signals may have a stronger signal strength than BSHG signals.

The terms "third harmonic generation" and "THG," as used herein, generally refer to a nonlinear optical process in which photons interacting with a nonlinear material are effectively "combined" to form new photons with about three times the energy, and therefore about three times the frequency and about a third ($\frac{1}{3}$) the wavelength of the initial photons.

The term "polarized light," as used herein, generally refers to light with waves oscillating in one plane. Unpolarized light can generally refer to light with waves oscillating in more than one plane.

The term "contrast enhancing agent," as used herein, generally refers to any agent such as but not limited to fluorophores, metal nanoparticles, nanoshell composites and semiconductor nanocrystals that can be applied to a sample to enhance the contrast of images of the sample obtained using optical imaging techniques. Fluorophores can be antibody targeted fluorophores, peptide targeted fluorophores, and fluorescent probes of metabolic activity. Metallic nanoparticles can comprise metals such as gold and silver that can scatter light. Nanoshell composites can include nanoparticles comprising a dielectric core and metallic shell. Semiconductor nanocrystals can include quantum dots, for example quantum dots containing cadmium selenide or cadmium sulfide.

The term "monochromatic," as used herein, generally refers to colors of a single hue.

The term "polychromatic," as used herein, generally refers to two or more colors.

The terms "in real-time" and "real-time" may be used interchangeably and, as used herein, generally refer to immediate, rapid, not requiring operator intervention, automatic, and/or programmed. Real-time may include, but is not limited to, measurements in femtoseconds, picoseconds, nanoseconds, milliseconds, as well as longer, and optionally shorter, time intervals.

The terms "field of view" or "FOV," as used herein, generally refers to a two-dimensional imaging space that may be visualized from a single insertion of the optical element.

The terms "local" or "locally" may be used interchangeably and, as used herein, generally refer to the area disposed adjacent to the probe. Local may refer to the area or tissue immediately adjacent to the probe (e.g., tissue contacting the probe) or tissue within a distance of less than or equal to about 5 millimeters (mm), 4 mm, 3 mm, 2 mm, 1 mm, 0.5 mm, 0.25 mm, or less. In an example, local refers to a distance of less than or equal to about 1 mm from the probe. In systems with one or more probes, local may refer to the tissue disposed between the probes and/or adjacent to the probes.

Optical Techniques for Detecting Muscle Tissue

The present disclosure provides optical techniques that may be used for detecting muscle tissue and muscle tissue diseases. Optical imaging techniques can display different types of muscle tissue including, but not limited to, myofibrils, sarcomeres, and collagen. Optical imaging techniques may allow for the detection and visualization of individual motor units and sarcomeres in vivo and in real-time. For example, optical techniques may be used to measure sarcomere length and to detect motor unit recruitment. Optical imaging techniques may be minimally or non-invasive. Minimally invasive techniques may include insertion of a probe, such as a needle, into muscle tissue. Non-invasive optical techniques may include techniques that do not puncture the muscle tissue. Non-limiting examples of optical imaging techniques for identifying muscle tissues and muscle tissue diseases include multiphoton microscopy, autofluorescence microscopy, polarized light microscopy, confocal microscopy, Raman spectroscopy, optical coherence tomography, and ultrasonography.

Multiphoton microscopy (MPM) can be used to image intrinsic molecular signals in living specimens, such as the muscle tissue of a patient. In MPM, a sample is illuminated with light at wavelengths longer than the normal excitation wavelength, for example twice as long or three times as long. MPM can include second harmonic generation microscopy (SHG) and third harmonic generation microscopy (THG). Third harmonic generation may be used to image nerve tissue. Second harmonic generation signals may be divided into two signal types, backward SHG (BSHG) signals and forward SHG (FSHG) signals. Backward second harmonic generation signals are optical signals that contact tissue, such as muscle tissue, and are directed back towards the light source. BSHG signals may not phase match after contacting tissue and, therefore, signals may constructively or destructively interfere. Constructive interference of BSHG signals may occur during analysis of thin specimens and not during analysis of thick specimens. Destructive interference of BSHG may reduce signal strength. Forward second harmonic generation signals may phase match and, therefore, have higher signal strengths than BSHG.

Forward second harmonic generation signals may have higher signal strength and a higher signal-to-noise ratio than BSHG signals. FSHG signals may generate higher qualities images than BSHG signals. Generated high quality images may have reduced noise, improved contrast, improved brightness, and improved contrast between types of tissues. Different types of tissues may generate varying proportions of BSHG and FSHG. The relative proportions of generated FSHG signals and BSHG signals may provide a means to selectively identify different types of tissues. Generated images from FSHG signals may therefore portray tissues that generate more FSHG signals than BSHG signals more prominently and provide a mechanism to selectively image those tissues. For example, sarcomeres may generate stronger FSHG signals than BSHG signals and collagen may generate both strong FSHG and BSHG signals. Therefore, collecting and using FSHG signals for imaging tissue may allow for sarcomeres to appear brighter and with higher contrast than collagen and collecting and using BSHG signals for imaging may allow for collagen to appear brighter and with higher contrast than sarcomeres. In this example, imaging tissue using FSHG signals may allow for the generation of higher quality images with respect to muscle tissue (e.g., sarcomeres). For example, FSHG may be used to identify muscle tissue (e.g., sarcomeres) at an intensity that is at least 5%, 10%, 20%, 30%, 40%, 50%, 60%, 70%, 80%, 90%, or greater than an intensity of non-muscle tissue (e.g., collagen).

In some examples, BSHG and FSHG signals may be collected. A first probe may be used to direct light to a tissue comprising muscle tissue. The first probe may be used to collect BSHG signals. See, e.g., U.S. Patent Publication No. 2015/0141846, which is entirely incorporated herein by reference. A second probe separate from the first probe may be used to collect FSHG signals. The image may be generated from signals from the first probe (e.g., BSHG signals), the second probe (e.g., FSHG signals), or both the first probe and the second probe.

Autofluorescence microscopy can be used to image biological molecules (e.g., fluorophores) that are inherently fluorescent. Non-limiting examples of endogenous biological molecules that are autofluorescent include nicotinamide adenine dinucleotide (NADH), NAD(P)H, flavin adenine dinucleotide (FAD), collagen, retinol, and tryptophan and the indoleamine derivatives of tryptophan. Changes in the fluorescence level of these fluorophores, such as with tumor progression, can be detected optically. Changes may be associated with altered cellular metabolic pathways (NADH, FAD) or altered structural tissue matrix (collagen).

Polarized light can be used to evaluate biological structures and examine parameters such as cell size and refractive index. A large variety of tissues may exhibit birefringence, such as eye cornea and sclera, cartilage, tendon, muscle, myocardium, nerve, and more. Such materials may exhibit different refractive indexes based on the angle with which they interact with light. Refractive index can provide information regarding the composition and organizational structure of cells, for example cells in a tissue sample.

Optical coherence tomography may also be used to examine muscle tissue. Optical coherence tomography is based on interferometry in which a laser light beam is split with a beam splitter, sending some of the light to the sample and some of the light to a reference. The combination of reflected light from the sample and the reference can result in an interference pattern which can be used to determine a reflectivity profile providing information about the spatial dimensions and location of structures within the sample. Current, commercial optical coherence tomography systems have lateral resolutions of about 10 to 15 micrometer (µm), with depth of imaging of about 1 millimeter (mm) or more. Although this technique can rapidly generate 3-dimensional (3D) image volumes that reflect different layers of tissue components (e.g., cells, connective tissue, etc), the image resolution (e.g., similar to the ×4 objective of a microscope) may not be sufficient for routine detection and diagnosis of muscle tissue.

Ultrasound may also be used to examine muscle tissue. Ultrasound can be used to assess and diagnose soft tissue conditions such as sprains, strains, and tears. Ultrasonography may also be useful in detecting and measuring muscle atrophy through morphometry measurements. However, ultrasonography may be limited in detecting individual tissue components. It may be used for noninvasive assessment of characteristics, such as morphology and for proxy muscle quality measurements.

Methods for identifying muscle tissue and muscle tissue diseases disclosed herein may comprise one or more of multiphoton microscopy, autofluorescence microscopy, polarized light microscopy, confocal microscopy, Raman spectroscopy, optical coherence tomography, and ultrasonography. In some cases, a method for identifying muscle tissue and muscle tissue diseases comprises autofluorescence microscopy and multiphoton microscopy. As an alternative, a method for identifying muscle tissue and muscle tissue diseases comprises autofluorescence microscopy, multiphoton microscopy, and polarized light microscopy. Both second harmonic generation microscopy and third harmonic generation microscopy may be used. In some cases, one of second harmonic generation microscopy and third harmonic generation microscopy is used. Both forward and backward second harmonic generation microscopy may be used. In some cases, one of forward and backward second harmonic generation may be used.

Apparatus for Identifying a Muscle Tissue Disease

In an aspect, the present disclosure provides an apparatus for identifying a muscle tissue of a subject. The apparatus may comprise a light source, an optical element comprising a first probe and a second probe, a collection unit, and a computer controller. The light source may generate a beam of light. The first probe may be an excitation probe. The excitation probe may transmit the beam of light from the light source to a tissue. The beam of light, upon contacting the tissue, may generate signals intrinsic to a property of the tissue. The second probe may be a collection probe. The collection probe may collect the signals generated by contacting the beam of light with the tissue. The computer controller may be programmed to direct the light source to generate a beam of light. The computer controller may be programmed to generate an image of the muscle tissue from the collected signals.

Figure 1B:
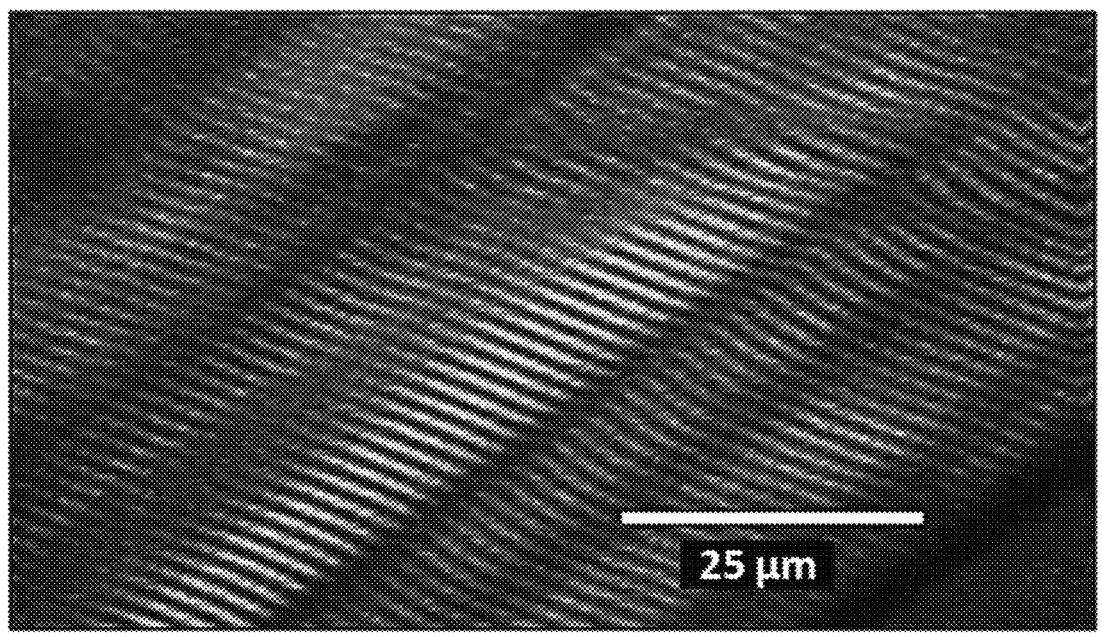
Figure 1C:
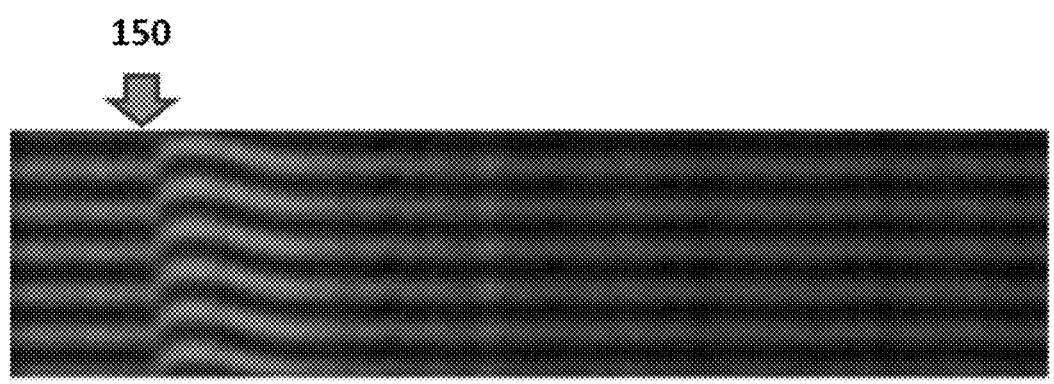

FIG. 1A shows an example apparatus for identifying a muscle tissue of a subject. The example apparatus comprises a laser source 105 that directs a beam of light 130 through a polarizer 110, a dichroic mirror 115 and a microscope objective 120 through a probe 125 to the muscle tissue of a subject. The beam of light 130 may contact the tissue of the subject and generate a signal 135. The signal 135 may be collected by the probe 125 and pass through the microscope objective 120 to the angled dichroic mirror 115. The microscope objective 120 may be telecentric. The signal 135 may reflect off of the dichroic mirror 115 and be directed through a filter to a photomultiplier tube (PMT) detector 145. The signal 135 that reaches the PMT detector 145 may be used to generate images of the muscle tissue. FIG. 1B shows a representative image generated with collected SHG signals. The image is of striated muscle tissue and the sarcomeres of the muscle tissue may be visible. Sarcomeres may be imaged via SHG signals and myosin autofluorescence with an accuracy of approximately 20 nanometers (nm) to 50 nm. The field of view of the image may include between about twenty and fifty sarcomeres. The field of view of the image may include greater than or equal to about 5, 10, 20, 30, 40, 50, 60, 70, 80, 90, 100, or more sarcomeres. In one example, the muscle tissue may be stimulated during imaging. FIG. 1C shows a representative image of stimulated muscle tissue. The muscle tissue may be stimulated by electrical impulse 150. The image shows striated muscle tissue undergoing twitch contraction of a motor unit. The contraction may be seen in the non-linear striation of the tissue.

Figure 2A:
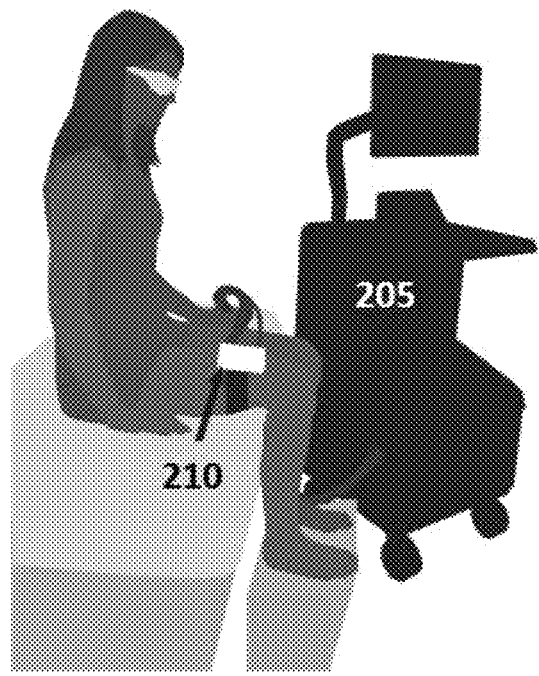
FIGS. 2A-2B show an overview of the system function.
Figure 2B:
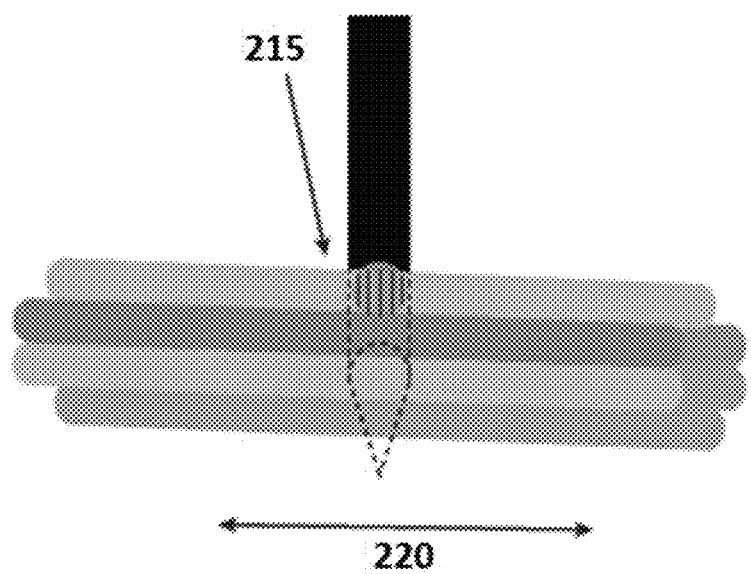

The apparatus for identifying muscle tissue may be a portable unit. The unit may comprise a handheld device and a tower. FIG. 2A shows an illustration of a portable apparatus being used to image muscle tissue in the leg of a subject. The portable apparatus may include a tower 205 and a handheld device 210. The tower 205 may include a display, such as a computer monitor, a light source, a collection unit, and a computer controller. The handheld device 210 may include one or more optical elements and a microscope. The optical elements may comprise one or more probes. The portable apparatus may additionally include a stimulation device. The stimulation device may comprise electrodes that may electrically stimulate the muscle tissue of a subject. The stimulation may be a general stimulation or may be a directional stimulation. Directional stimulation may recruit motor units in a selected direction. The stimulation may be a local stimulation. Local stimulation may stimulate tissue within a distance of less than or equal to about 5 mm, 4 mm, 3 mm, 2 mm, 1 mm, 0.5 mm, 0.25 mm, or less of the probe. The computer controller may be programmed to control the emission of the light source, to direct the electrical stimulation, and to generate images of the muscle tissue. The handheld device may further include optical components for scanning the tissue. The optical components for scanning the tissue may include scanners that act in the horizontal direction (e.g., parallel to the outer plane of the tissue) or in the vertical direction (e.g., orthogonal to the outer plane of the tissue). The horizontal scanning may generate a two-dimensional image and the vertical scanning may generate a depth profile (e.g., into the tissue). FIG. 2B shows an illustration of the muscle tissue 215 in relation to the probe. The probe may be perpendicular or substantially perpendicular to the fiber direction 220 of the muscle tissue 215. Alternatively, or in addition to, the probe may not be perpendicular to the fiber direction of the muscle tissue.

The handheld device may comprise a portable housing. The housing can have a footprint of greater than or equal to about 0.1 $ft^2$, 0.2 $ft^2$, 0.3 $ft^2$, 0.4 $ft^2$, 0.5 $ft^2$, or 1 $ft^2$. As an alternative, the housing can have a footprint that is less than or equal to about 1 $ft^2$, 0.5 $ft^2$, 0.4 $ft^2$, 0.3 $ft^2$, 0.2 $ft^2$, or 0.1 $ft^2$. The housing may weigh less than or equal to about 5 pounds (lbs), 4 lbs, 3 lbs, 2 lbs, 1 lb, 0.5 lb, or less. In an example, the portable housing is the size of a briefcase or laptop computer.

The muscle tissue images may be generated in real-time. The real-time images may be discrete images. Alternatively, or in addition to, the handheld device may use the optical element to take a video (e.g., real-time video) and the images may be extracted from the video. Alternatively, or in addition two, images collected in real-time over multiple time points and may be compiled or combined into a video. For example, the image is generated while the optical element transmits a beam of light from the light source towards the muscle tissue. The image may be generated at a frame rate of greater than or equal to about 1 frames per second (FPS), 2 FPS, 3 FPS, 4 FPS, 5 FPS, 10 FPS, or greater. Frame rate generally refers to the rate at which an imaging device displays consecutive images called frames. An image frame can provide a two-dimensional image of muscle tissue. The image frame may be a quadrilateral with any suitable dimensions. An image frame may be rectangular, in some cases with equal sides (e.g., square), for example, depicting a 200 micrometers (μm) by 200 μm two-dimensional image of the muscle tissue. The image frame may depict a two-dimensional of the muscle tissue having dimensions of about 50 μm by 50 μm, 100 μm by 100 μm, 150 μm by 150 μm, 200 μm by 200 μm, 250 μm by 250 μm, 300 μm by 300 μm, or greater. In some cases, the image frame may not have equal sides (e.g., rectangle).

The identified muscle tissue and muscle tissue characteristics may include myofibrils, sarcomeres, collagen, motor unit recruitment, or any combination thereof. The tissue identified may also include non-muscle tissue including, but not limited to, connective tissue, nervous tissue, epithelial tissue, or mineralized tissue. Muscle tissue diseases that may be identified and monitored may include, but are not limited to, sarcopenia, amyotrophic lateral sclerosis, muscular dystrophy, or any muscular degenerative disease.

An handheld device may comprise an optical element comprising one or more probes that make direct contact with the muscle tissue to image the muscle structure. The handheld device may also comprise a microscope. The microscope may be a handheld microscope. The handheld device may comprise multiple refractive lenses, such as relay lenses, collimating lenses, and field lenses, which may be used to focus the beam of light from a light source to a small spot within the muscle tissue. The small spot of focused light can, upon contacting the muscle tissue, generates endogenous tissue signals, such as second harmonic generation, 2-photon autofluorescence, third harmonic generation, coherent anti-stokes Raman spectroscopy, or other nonlinear multiphoton generated signals. In an example, generated signal may be acoustic signals or optoacoustic signals.

Figure 3:
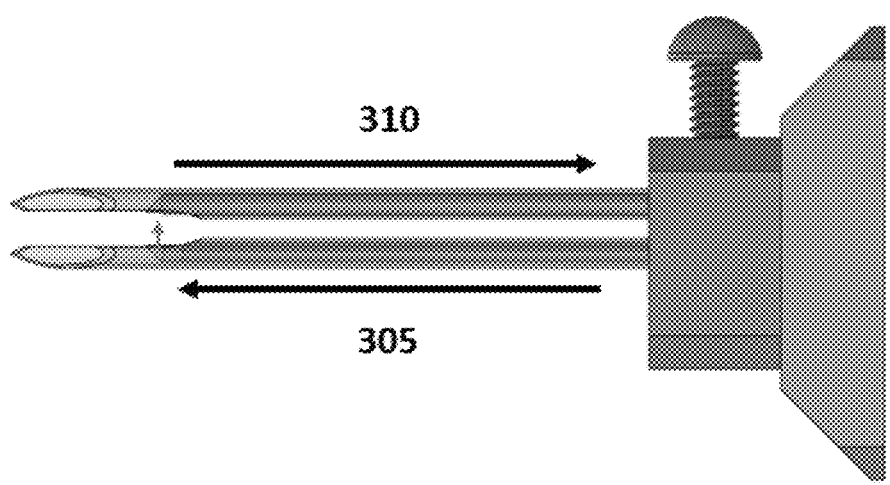
FIG. 3 is an illustration of an example dual probe optical element.

The probe may be a single probe or a dual probe. The probe may comprise one or more needles. The probe may comprise one or more light pipe needles. The probe may penetrate a body of a subject. The probe may penetrate a tissue of a subject. The probe may penetrate a muscle tissue of the subject. The probe may be positioned perpendicular to the muscle fibers during imaging. Alternatively, or in addition to, the probe may not be positioned perpendicularly to the muscle fibers during imaging. In one example, the probe is a dual probe. FIG. 3 is an illustration of an optical element comprising a dual probe. One of the probes in the dual probe system may be an excitation probe. The excitation probe 305 may direct a beam of light from the light source to the muscle tissue. The other probe in the dual probe optical element may be a collection probe 310. The collection probe 310 may collect the signals generated when the beam of light contacts the muscle tissue. The excitation and collection probe may be separated by a distance of less than or equal to about 5 millimeters (mm), 4 mm, 3 mm, 2 mm, 1 mm, 0.75 mm, 0.5 mm, 0.25 mm, or less. In one example, the excitation 305 and collection 310 probe may be separated by a distance of about 1 mm or less. The tip of the probe may extend greater than or equal to about 0.5 mm, 1 mm, 2 mm, 3 mm, 4 mm, 5 mm, 6 mm, 7 mm, 8 mm, 9 mm, 1 centimeter (cm), 2 cm, or more into the tissue of the subject. The collected signals may be autofluorescence signals, second harmonic generation signals, third harmonic generation signals, or any combination thereof. In one example, the signals are second harmonic generation signals. In one example, the signals are forward second harmonic generation signals.

Figure 4A:
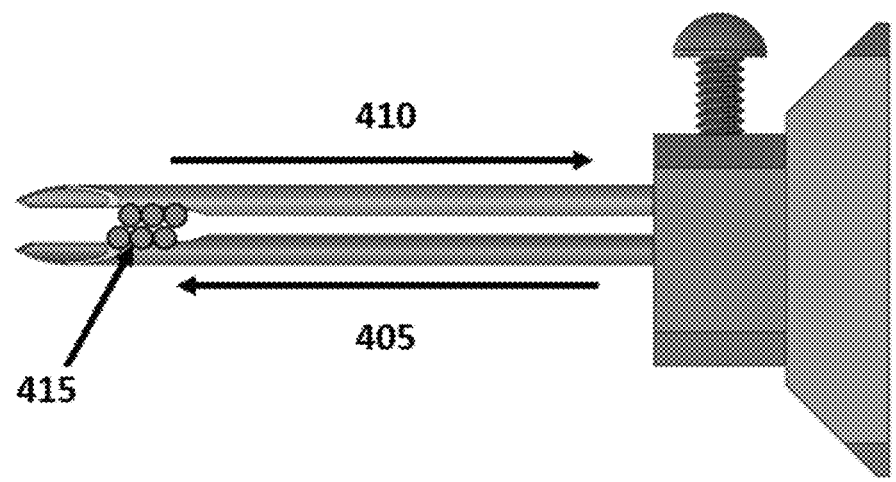
FIG. 4A is an illustration of an example dual probe optical element with muscle fibers positioned between the dual probe tips.
Figure 4B:
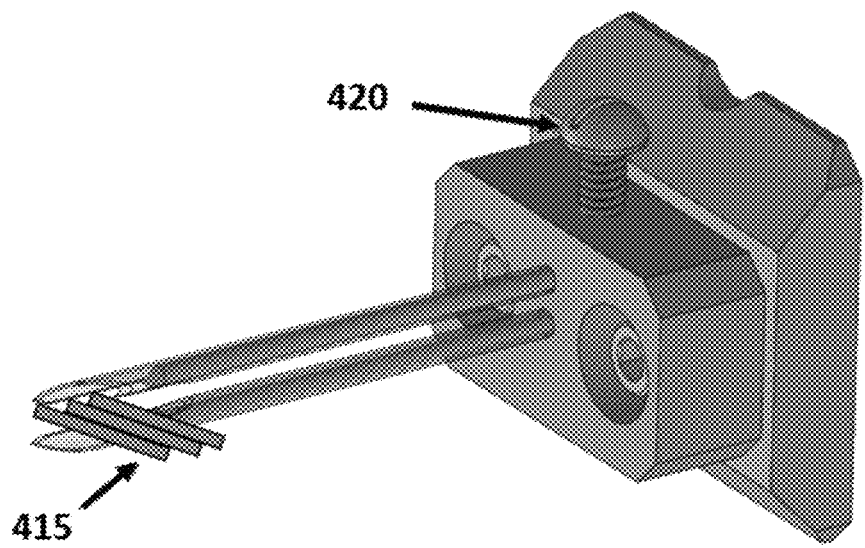
FIG. 4B is an alternate view of an example dual probe optical element with muscle fibers positioned between the dual probe tips.

FIGS. 4A and 4B show alternative views of an optical element comprising a dual probe with muscle fibers 415 positioned between the probe tips. In one example, the excitation probe 405 emits a beam of light to the muscle fibers positioned between the probes. The beam of light may generate FSHG signals upon contact with the muscle tissue 415 and the collection probe 410 may collect the FSHG signals. In one example, the dual probe optical element is electrically connected to a stimulation device through a stimulus wire connector 420. During operation, the stimulation device may provide a voltage to the muscle tissue 415. During stimulation, the excitation probe, the collection probe, or both the excitation and collection probes may act as a cathode for the stimulation. During stimulation, the excitation probe, the collection probe, or both the excitation probe and collection probe may act as an anode for the stimulation device. In one example, both probes of the dual probe optical element are in electrical communication with the stimulation device and deliver a voltage. In one example, one of the probes of the dual probe optical element is in electrical communication with the stimulation device and delivers a voltage. In one example, one of the probes of the dual probe optical element is in electrical communication with the stimulation device and delivers a voltage while the other probe is used to sense biologic electrical signals. In one example, both probes of the dual probe optical element are used to sense biological signals in a differential sensing arrangement.

The beam of light may be a single beam of light. The beam of light may be polarized. The beam of light may be non-polarized. The beam of light may be pulsed. The pulses may mitigate artifacts due to motion of the muscle tissue. The pulses may be ultrashort pulses of light. Ultrashort pulses of light can be emitted from an ultrashort pulse laser (herein also referred to as an "ultrafast pulse laser"). Ultrashort pulses of light can have high peak intensities leading to nonlinear interactions in various materials. Ultrashort pulses of light generally refer to light having a full width of half maximum (FWHM) on the order of femtoseconds or picoseconds. In some examples, an ultrashort pulse of light has a FWHM of greater than or equal to about 1 femtosecond, 10 femtoseconds, 100 femtoseconds, 1 picosecond, 100 picoseconds, 1000 picoseconds, or more. Ultrashort pulses of light can be characterized by several parameters including pulse duration, pulse repetition rate, and average power. Pulse duration generally refers to the FWHM of the optical power as a function of time. Pulse repetition rate generally refers to the frequency of the pulses or the number of pulses per second. Non-limiting examples of ultrashort pulse laser technologies include Ti:Sapphire lasers, mode-locked diode-pumped lasers, mode-locked fiber lasers, and mode-locked dye lasers. A Ti:Sapphire laser is a tunable laser using a crystal of sapphire ($Al_2O_3$) that is doped with titanium ions as a lasing medium (e.g., the active laser medium which is the source of optical gain within a laser). Lasers, for example diode-pumped laser, fiber lasers, and dye lasers, can be mode-locked by active mode locking or passive mode locking, to obtain ultrashort pulses. A diode-pumped laser is a solid-state laser in which the gain medium comprises a laser crystal or bulk piece of glass (e.g., ytterbium crystal, ytterbium glass, and chromium-doped laser crystals). Although the pulse durations may not be as short as those possible with Ti:Sapphire lasers, diode-pumped ultrafast lasers can cover wide parameter regions in terms of pulse duration, pulse repetition rate, and average power. Fiber lasers based on glass fibers doped with rare-earth elements such as erbium, ytterbium, neodymium, dysprosium, praseodymium, thulium, or combinations thereof can also be used. In some cases, a dye laser comprising an organic dye, such as rhodamine, fluorescein, coumarin, stilbene, umbelliferone, tetracene, malachite green, or others, as the lasing medium, in some cases as a liquid solution, may be used.

The light source that provides ultrashort pulses of light can be a wavelength-tunable, ultrashort-pulsed Ti:Sapphire laser. A Ti:Sapphire laser can be a mode-locked oscillator, a chirped-pulse amplifier, or a tunable continuous wave laser. A mode-locked oscillator can generate ultrashort pulses with a duration between about a few picoseconds and about 10 femtoseconds, and in some cases about 5 femtoseconds. The pulse repetition frequency can be greater than or equal to about 10 megahertz (MHz), 20 MHz, 30 MHz, 40 MHz, 50 MHz, 60 MHz, 70 MHz, 80 MHz, 90 MHz, or more. The pulse repetition frequency may be between about 10 MHz and 20 MHz, 10 MHz and 30 MHz, 10 MHz and 40 MHz, 10 MHz and 50 MHz, 10 MHz and 60 MHz, 10 MHz and 70 MHz, 10 MHz and 80 MHz, of 10 MHz and 90 MHz. In an example, the pulse repetition frequency is between about 70 MHz and 90 MHz. The term 'chirped-pulse' generally refers to a special construction that can prevent the pulse from damaging the components in the laser. In a 'chirped-pulse' laser, the pulse can be stretched in time so that the energy is not all located at the same point in time and space, preventing damage to the optics in the amplifier. The pulse can then be optically amplified and recompressed in time to form a short, localized pulse. These devices can generate ultrashort, ultra-high-intensity pulses with a duration of greater than or equal to about 10 femtoseconds, 20 femtoseconds, 30 femtoseconds, 40 femtoseconds, 50 femtoseconds, 60 femtoseconds, 70 femtoseconds, 80 femtoseconds, 90 femtoseconds, 100 femtoseconds, or more. The duration of the pulses may be less than or equal to about 100 femtoseconds, 90 femtosecond, 80 femtoseconds, 70 femtoseconds, 60 femtoseconds, 50 femtoseconds, 40 femtoseconds, 30 femtoseconds, 20 femtoseconds, 10 femtoseconds, or less. The duration of the pulses may be between about 10 femtoseconds and 20 femtoseconds, 10 femtoseconds and 30 femtoseconds, 10 femtoseconds and 40 femtoseconds, 10 femtoseconds and 50 femtoseconds, 10 femtoseconds and 60 femtoseconds, 10 femtoseconds and 70 femtoseconds, 10 femtoseconds and 80 femtoseconds, 10 femtoseconds and 90 femtoseconds, or 10 femtoseconds and 100 femtoseconds. In an example, the duration of the pulses is between about 20 femtoseconds and about 100 femtoseconds. The duration of the pulses may be constant over time or may modulate over time.

Ultrashort pulses of light can be produced by gain switching. In gain switching, the laser gain medium is pumped with, e.g., another laser. Gain switching can be applied to various types of lasers including gas lasers (e.g., TEA carbon dioxide lasers).

Adjusting the pulse repetition rate can, in some cases, be more easily accomplished with gain-switched lasers than mode-locked lasers, as gain-switching can be controlled with an electronic driver without changing the laser resonator setup. In some cases, a pulsed laser can be used for optically pumping a gain-switched laser. For example, nitrogen ultraviolet lasers or excimer lasers can be used for pulsed pumping of dye lasers. In some cases, Q-switching can be used to produce ultrafast pulses of light.

An ultra-fast pulse laser may produce pulses of light with pulse durations less than 500 femtoseconds, 450 femtoseconds, 400 femtoseconds, 350 femtoseconds, 300 femtoseconds, 250 femtoseconds, 200 femtoseconds, 150 femtoseconds, 100 femtoseconds, 50 femtoseconds, 25 femtoseconds, or shorter. In some cases, the pulse duration is about 150 femtoseconds. The pulse repetition frequency of an ultra-fast pulse laser can be at least 10 MHz, 20 MHz, 30 MHz, 40 MHz, 50 MHz, 60 MHz, 70 MHz, 80 MHz, 90 MHz, 100 MHz, or greater. In some cases, the pulse repetition frequency is about 80 MHz.

Fibrils and cellular structures in muscle tissue can interact with the pulses of the single beam of light in a wavelength dependent manner and generate signals that relate to intrinsic properties of the muscle tissue. The signals generated can be used to evaluate sarcomere length, sarcomere displacement, motor unit recruitment, and contraction and relaxation times. The subset of the signals generated and collected can include at least one of second harmonic generation (SHG) signals, third harmonic generation (THG) signals, polarized light signals, and autofluorescence signals. Additionally, SHG signals may include forward SHG signals, backward SHG signals, or both. Higher harmonic generation microscopy (HHGM) (e.g., second harmonic generation and third harmonic generation), based on nonlinear multiphoton excitation, can be used to examine cellular structures in live and fixed tissues. SHG generally refers to a nonlinear optical process in which photons with about the same frequency interact with a nonlinear material and effectively "combine" to generate new photons with about twice the energy, and therefore about twice the frequency and about half ($\frac{1}{2}$) the wavelength of the initial photons. Similarly, THG generally refers to a nonlinear optical process in which photons with about the same frequency interact with a nonlinear material and effectively "combine" to generate new photons with about three times the energy, and therefore about three times the frequency and about one-third ($\frac{1}{3}$) the wavelength of the initial photons. Second and third harmonic generation (SHG, THG) of ordered endogenous molecules, such as but not limited to collagen, microtubules, and muscle myosin, can be obtained without the use of exogenous labels and provide detailed, real-time optical reconstruction of molecules including fibrillar collagen, myosin, microtubules as well as other cellular information such as membrane potential and cell depolarization. The ordering and organization of proteins and molecules in a tissue, for example collagen type I and II, myosin, and microtubules, can generate, upon interacting with light, signals that can be used to evaluate the diseased state of a tissue. SHG signals can be used to detect changes such as changes in collagen fibril/fiber structure that may occur in diseases including cancer, fibrosis, and connective tissue disorders. Various biological structures can produce SHG signals. In some cases, the labeling of molecules with exogenous probes and contrast enhancing agents, which can alter the way a biological system functions, may not be necessary. In some cases, methods herein for identifying a muscle tissue of a subject are performed in the absence of administering a contrast enhancing agent to the subject.

Another type of signal that may be generated and collected for use identifying muscle tissue is autofluorescence. Autofluorescence generally refers to light that is naturally emitted by certain biological molecules, such as proteins, small molecules and/or biological structures. Muscle tissue and cells can comprise various autofluorescent proteins and compounds. Well-defined wavelengths can be absorbed by chromophores, such as endogenous molecules, proteins, water, and adipose that are naturally present in cells and tissue. Non-limiting examples of autofluorescent fluorophores that can be found in tissues include polypeptides and proteins comprising aromatic amino acids such as Trp, Tyr, and Phe which can emit in the UV range and vitamin derivatives which can emit at wavelengths in a range of about 400 nm to 600 nm, including retinol, riboflavin, the nicotinamide ring of NAD(P)H derived from niacin, and the pyridolamine crosslinks found in elastin and some collagens, which are based on pyridoxine (vitamin B6).

In some cases, an optical probe can be used to transmit pulses of polarized light towards a muscle tissue. Polarized light can be used to generate contrast in biological specimens from birefringent molecules such as cellulose and starch. Polarized light can be used to examine parameters such as cell size and refractive index. Refractive index can provide information, such as information regarding the composition of cells and organizational structure of cells, for example cells in a tissue sample.

A wavelength of the beam of light may be greater than or equal to about 400 nanometers (nm), 450 nm, 500 nm, 550 nm, 600 nm, 650 nm, 700 nm, 750 nm, 800 nm, 850 nm, 900 nm, 950 nm or longer. In some cases, the wavelength of the pulses of light is between about 700 nm and 900 nm, between about 725 nm and 875 nm, between about 750 nm and 850 nm, or between about 775 nm and 825 nm. Multiple wavelengths may also be used. When multiple wavelengths of light are used, the wavelengths can be centered at about 400 nm, 450 nm, 500 nm, 550 nm, 600 nm, 650 nm, 700 nm, 750 nm, 800 nm, 850 nm, 900 nm, 950 nm or longer with a bandwidth of greater than or equal to about 10 nm, 20 nm, 30 nm, 40 nm, 50 nm, 75 nm, 100 nm, 125 nm, 150 nm, 175 nm, 200 nm, 225 nm, 250 nm, 275 nm, 300 nm or longer. For example, the wavelengths can be centered at about 780 nm with a bandwidth of about 50 nm (e.g., about ((780−(50/2))=755 nm) to about ((780+(50/2))=805 nm)).

The subset of signals generated as a result of the beam of light may be collected the collection unit. The collection unit may comprise a photodetector, such as a photomultiplier tube (PMT) sensor, photodiode, avalanche photodiode, charge-coupled device (CCD), charge-injection device (CID), and complementary-metal-oxide-semiconductor detector (CMOS). The power and gain of the PMT may be modulated to enhance the image quality. The collection unit may have a single PMT sensor or may have multiple PMT sensors. For example, the SHG portion of the signal may go to a first PMT sensor (PMT 1). The autofluorescence portion of the signal may split into two channels with one channel going to a second PMT sensor (PMT 2) and the second channel going to a third PMT sensor (PMT 3). Light entering each PMT may pass through an optical filter to remove background noise, back reflected light from the illuminating laser pulses, and mixing of light between PMT channels. Each PMT may provide a digital image of the intensity of its respective signal component. The computer processor may then be programmed to build a pixel by pixel image from each channel as the excitation is scanned.

Optical filters can be used to collect the subset of signals, for example light corresponding to autofluorescence signals, second harmonic generation signals, and third harmonic generation signals. Optical filters can selectively transmit light of different wavelengths and may comprise a pane glass or plastic device in the optical path. Optical filters may be bandpass filters, which reflect light that falls out of the bandpass range. Bandpass filters can reflect at least about 10%, 20%, 30%, 40%, 50%, 60%, 70%, 80%, 90% or more of light that falls outside of the bandpass range. In some cases, optical filters can be used to collect the subset of signals, such as second harmonic generation signals, third harmonic generation signals, signals from polarized light, and autofluorescence signals.

In some cases, these signals may be collected in the presence of ambient light. Ambient light can refer to normal room lighting, such as provided by various types of electric lighting sources including incandescent light bulbs or lamps, halogen lamps, gas-discharge lamps, fluorescent lamps, light-emitting diode (LED) lamps, and carbon arc lamps, in a medical examination room or an operating area where a surgical procedure is performed.

The signals may be collected and images generated during stimulation of the muscle tissue. Alternatively, or in addition to, the signals may be collected and imaged generated before stimulation, after stimulation, or both before and after stimulation. Muscle tissue stimulation may include stimulating the tissue with an electrical potential. The stimulation device may include greater than or equal to about 1, 2, 3, 4, 6, 8, 10, or more electrodes attached to a power source. In an example, the stimulation device includes four electrodes. Each of the electrodes may stimulate the tissue in a given direction or directionally stimulate the tissue. The electrodes may function as anodes, cathodes, or both anodes and cathodes during electrical stimulation. Additionally, the probe may function as a part of the stimulation device. The probe may function as an anode or cathode during electrical stimulation. The stimulation may be local to the probe. The muscle tissue may be stimulated with constant electrical potential. The constant electrical potential may be less than or equal to about 30 volts (V), 25 V, 20 V, 15 V, 10 V, 9 V, 8 V, 7 V, 6 V, 5 V, 4 V, 3 V, 2 V, 1 V, 0.5 V, or less. The muscle tissue may be stimulated with an increasing electrical potential. For example, electrical potential may begin at zero volts and linearly increase to greater than or equal to about 30 V. Alternatively, or in addition to, the stimulation electrical potential may begin at zero volts and non-linearly increase to greater than or equal to about 30 V. Muscle tissue may be stimulated with an electrical potential between about 0 V and 0.5 V, 0 V and 1 V, 0 V and 2 V, 0 V and 3 V, 0 V and 4 V, 0V and 5 V, 0V and 6 V, 0V and 7 V, 0V and 8 V, 0V and 9 V, 0V and 10 V, 0 V and 15 V, 0 V and 20 V, 0 V and 25 V, 0 V and 30 V, or more.

During stimulation, electrical potential may be applied constantly or in short pulses. The duration of stimulation may be less than or equal to about 5 seconds (s), 4 s, 3 s, 2 s, 1 s, 500 milliseconds (ms), 500 ms, 250 ms, 100 ms, 50 ms, or less. The duration of stimulation pulses may be for less than or equal to about 500 ms, 250 milliseconds (ms), 100 ms, 50 ms, 25 ms, 10 ms, 750 microseconds (µs), 500 µs, 250 µs, 100 µs, 50 µs, or less.

The collected signals can be processed by a programmed computer controller to generate two-dimensional images of the muscle tissue. The signals can be transmitted wirelessly to a programmed computer processor. As an alternative, the signals may be transmitted through a wired connection to a programmed computer controller. The signals or a subset of the signals relating to an intrinsic property of the muscle tissue can be used to generate a two-dimensional image with the aid of a programmed computer processor. The collected signals and/or generated image can be stored electronically. In some cases, the signals and/or images are stored until deleted by a user, such as a surgeon, physician, nurse or other healthcare practitioner. When used for diagnosis and/or treatment, the two-dimensional image may be provided to a user in real-time. A two-dimensional image provided in real-time can be used to measure sarcomere length, measure sarcomere displacement, measure motor unit recruitment, or motor unit contractility. Contractility may be defined as the tissue displacement per volt.

The image can comprise a monochromatic image displaying colors derived from a single base hue. As an alternative, the image can comprise a polychromatic image displaying more than one color. In a polychromatic image, multiple colors can be used to highlight different elements of a muscle tissue, such as a sarcomeres and collagen. The contrast can be adjusted in real-time to provide and/or enhance structure specific contrast. The contrast can be adjusted by a user (e.g., surgeon, physician, nurse or other healthcare practitioner) or a programmed computer processor may automatically optimize the contrast in real-time. In a polychromatic image, each color may be used to represent a specific subset of the signals collected, such as second harmonic generation signals, third harmonic generation signals, signals resulting from polarized light, and autofluorescence signals. Use of a two-dimensional image generated by the methods disclosed herein can allow a user to distinguish healthy tissue from non-healthy tissue. The image may be provided on a display in proximity to the doctor and/or patient such that the user can evaluate in real-time the tissue being examined. A display can be a screen associated with any computing device, such as a computer, television, or a mobile computing device such as a phone or tablet.

An apparatus for identifying muscle tissue of a subject may comprise an optical element. The optical element may transmit pulses of a single beam of light from a light source towards a muscle tissue. The pulses of a single beam of light, upon contacting the muscle tissue, can then generate signals that relate to an intrinsic property of the muscle tissue. The light source may comprise an ultra-fast pulse laser, such as a Ti:Sapphire laser. The ultra-fast pulse laser may generate pulse durations less than or equal to about 500 femtoseconds, 400 femtoseconds, 300 femtoseconds, 200 femtoseconds, 100 femtoseconds, 50 femtoseconds, 25 femtoseconds or less. The pulse repetition frequency of the ultrashort light pulses can be greater than or equal to about 10 MHz, 20 MHz, 30 MHz, 40 MHz, 50 MHz, 60 MHz, 70 MHz, 80 MHz, 90 MHz, 100 MHz, or greater.

The apparatus may comprise a mobile lens in optical communication with the optical probe. During use, the mobile lens may provide for focusing of the optical element with respect to the muscle tissue. The mobile lens of an apparatus can be translated to yield the plurality of different focal planes. The mobile lens may be coupled to an actuator that translates the lens. The actuator may be controlled by a programmed computer processor. The actuator can be a linear actuator, such as a mechanical actuator, a hydraulic actuator, a pneumatic actuator, a piezoelectric actuator, an electro-mechanical actuator, a linear motor, or combinations thereof. Mechanical actuators can operate by converting rotary motion into linear motion, for example by a screw mechanism, a wheel and axle mechanism, and a cam mechanism. A hydraulic actuator can involve a hollow cylinder comprising a piston and an incompressible liquid. A pneumatic actuator may be similar to a hydraulic actuator but involves a compressed gas instead of a liquid. A piezoelectric actuator can comprise a material which can expand under the application of voltage. As a result, piezoelectric actuators can achieve extremely fine positioning resolution, but may also have a very short range of motion. In some cases, piezoelectric materials can exhibit hysteresis which may make it difficult to control their expansion in a repeatable manner. Electro-mechanical actuators are similar to mechanical actuators except that the control knob or handle is replaced with an electric motor.

An apparatus for identifying muscle tissue may comprise optical filters. Optical filters, as described elsewhere herein, can be used to collect one or more specific subsets of signals that relate to one or more intrinsic properties of the muscle tissue. These optical filters can be coated glass or plastic elements which can selectively transmit certain wavelengths of light, such as autofluorescent wavelengths, and/or light with other specific attributes, such as polarized light. The optical filters can collect at least one of second harmonic generation (SHG) signals, third harmonic generation (THG) signals, polarized light signals, and autofluorescence signals.

Methods for Identifying Muscle Tissue Disease

In an aspect, a method for identifying a muscle tissue of a subject may comprise inserting an optical element into a tissue of a subject, transmitting a beam of light from a light source to the tissue, generating signals intrinsic to a property of the tissue, collecting the generated signals, and using a computer controller to generate at least one image of the tissue. The optical element may include a probe and a microscope that can attach to the probe. The probe may be a single probe or a dual probe. The microscope may be a handheld, portable microscope. The beam of light may be a single beam of light. The beam of light may be a pulsed beam of light. Upon contact with the tissue, the beam of light may generate signals intrinsic to properties of the tissue. The signals may include a single signal or a plurality of signals. In one example, a method for identifying a muscle tissue of a subject may further comprise electrically stimulating the muscle tissue with a stimulation device and collecting generated signals before, during, and after muscle stimulation. The computer controller may direct the light source to generate the beam of light. The computer controller may direct the stimulation device to stimulate the muscle tissue while simultaneously directing the beam of light to the tissue and collecting the signals generated. The computer controller may use the signals to generate a two-dimensional image of the muscle tissue. The two-dimensional image may be used to measure sarcomere length, measure sarcomere displacement during stimulation, measure motor unit recruitment, or contractility.

In an example, the beam of light is directed towards the tissue as a pulsed beam of light. The pulsed beam of light may mitigate artifacts due to motion of the muscle tissue. The pulsed beam of light may have a duration that is less than or equal to about 500 femtoseconds, 400 femtoseconds, 300 femtoseconds, 200 femtoseconds, 100 femtoseconds, 50 femtoseconds, 25 femtoseconds or less. The pulse repetition frequency of may be greater than or equal to about 10 MHz, 20 MHz, 30 MHz, 40 MHz, 50 MHz, 60 MHz, 70 MHz, 80 MHz, 90 MHz, 100 MHz, or greater.

A wavelength of the beam of light may be greater than or equal to about 400 nanometers (nm), 450 nm, 500 nm, 550 nm, 600 nm, 650 nm, 700 nm, 750 nm, 800 nm, 850 nm, 900 nm, 950 nm or longer. In some cases, the wavelength of the pulses of light is between about 700 nm and 900 nm, between about 725 nm and 875 nm, between about 750 nm and 850 nm, or between about 775 nm and 825 nm. Multiple wavelengths may also be used. When multiple wavelengths of light are used, the wavelengths can be centered at about 400 nm, 450 nm, 500 nm, 550 nm, 600 nm, 650 nm, 700 nm, 750 nm, 800 nm, 850 nm, 900 nm, 950 nm or longer with a bandwidth of greater than or equal to about 10 nm, 20 nm, 30 nm, 40 nm, 50 nm, 75 nm, 100 nm, 125 nm, 150 nm, 175 nm, 200 nm, 225 nm, 250 nm, 275 nm, 300 nm or longer. For example, the wavelengths can be centered at about 780 nm with a bandwidth of about 50 nm (e.g., about ((780−(50/2))= 755 nm) to about ((780+(50/2))=805 nm)).

The subset of signals generated as a result of the beam of light may be collected by a photodetector, such as a photomultiplier tube (PMT), photodiode, avalanche photodiode, charge-coupled device (CCD), charge-injection device (CID), and complementary-metal-oxide-semiconductor detector (CMOS). The power and gain of the PMT may be modulated to enhance the image quality. Optical filters can be used to collect the subset of signals, for example light corresponding to autofluorescence signals, second harmonic generation signals, and third harmonic generation signals. Optical filters can selectively transmit light of different wavelengths and may comprise a pane glass or plastic device in the optical path. Optical filters may be bandpass filters, which reflect light that falls out of the bandpass range. Bandpass filters can reflect at least about 10%, 20%, 30%, 40%, 50%, 60%, 70%, 80%, 90% or more of light that falls outside of the bandpass range. In some cases, optical filters can be used to collect the subset of signals, such as second harmonic generation signals, third harmonic generation signals, signals from polarized light, and autofluorescence signals.

Figure 5:
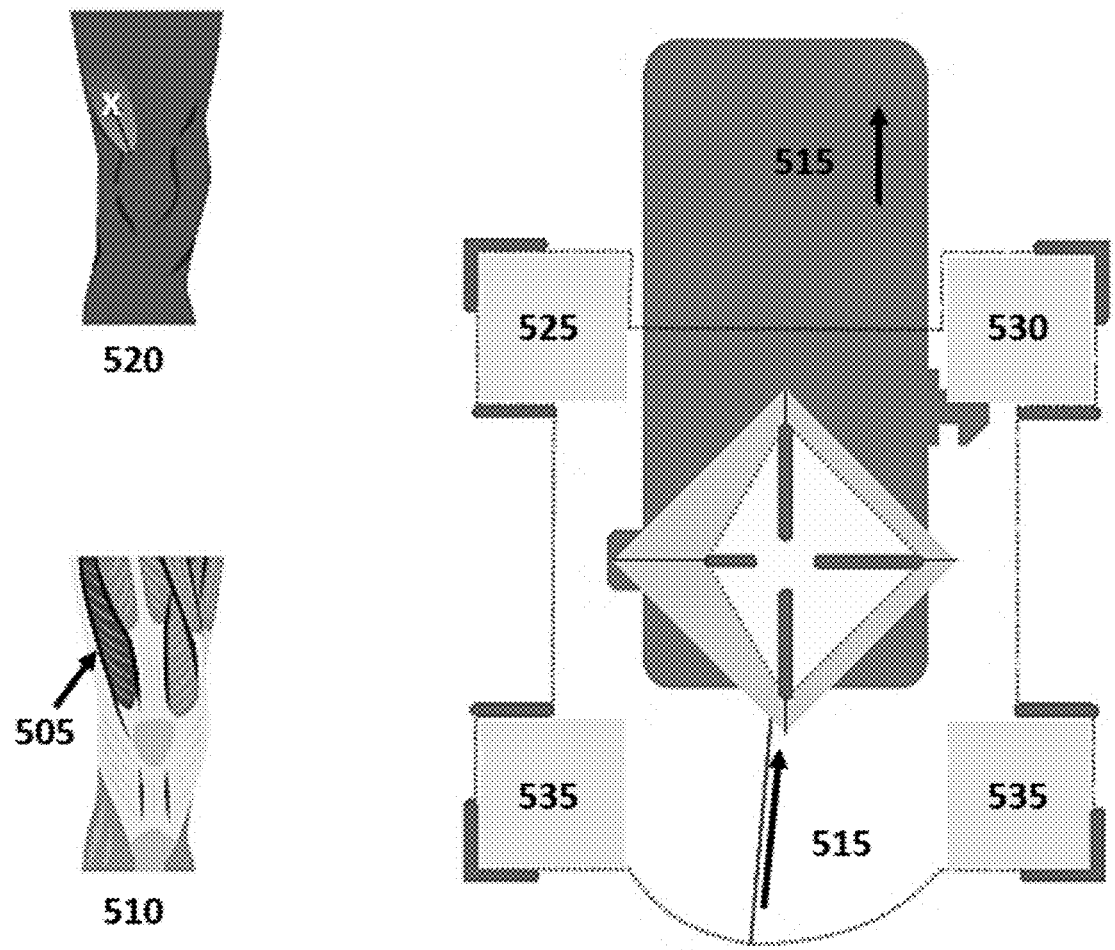
FIG. 5 is an illustration of example electrode positioning in reference to an optical element injection site.

Stimulation may be performed with the use of a stimulation device. A stimulation device may comprise multiple electrodes in electrical communication with the optical element. FIG. 5 is an example of electrode positioning for stimulating and imaging the vastus lateralis muscle 505, as shown in the muscle view diagram. In this example, four electrodes are positioned in a rectangle pattern around the optical probe and the optical probe is positioned perpendicular to the direction of the muscle fibers 515. The 'x' on the skin view diagram 520 shows an example probe injection site. Electrical stimulation may be provided by greater than or equal to 1, 2, 3, 4, 5, 6, 8, 10, or more electrodes. The electrode may generate an electrical current that flows through the muscle to the optical probe. The electrical current may flow to the excitation probe, the collection probe, or to both the excitation and collection probe. In an example, and as shown in FIG. 5, four electrodes may be used for electrical stimulation. The four electrodes may be placed in a proximal lateral 525, proximal medial 530, distal lateral 535, and/or distal medial 540 position of the optical probe.

Figure 6A:
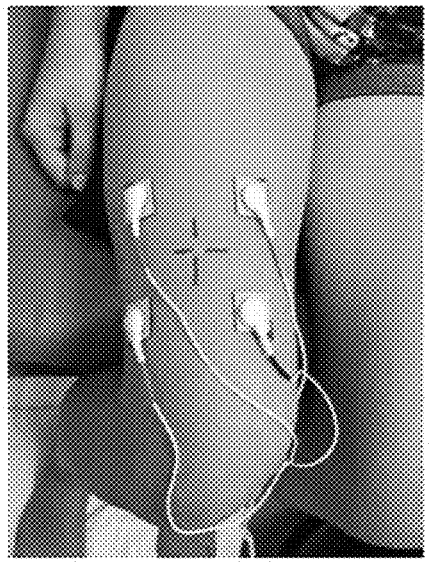
FIGS. 6A-6D are images of an example optical element setup.
Figure 6B:
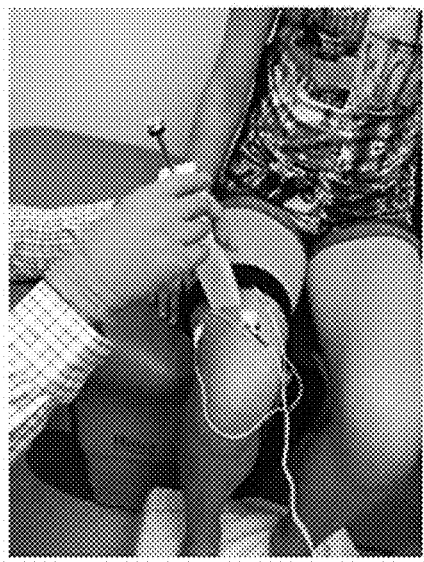
Figure 6C:
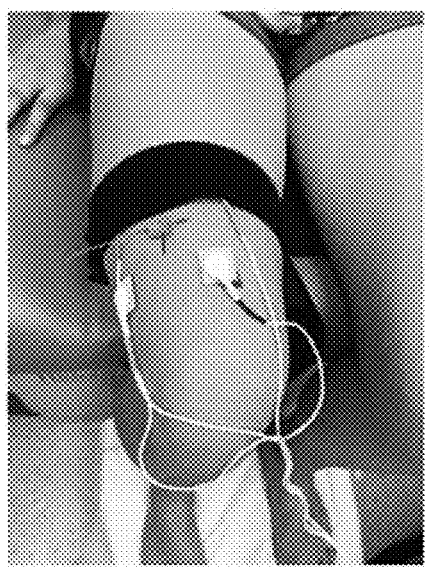
Figure 6D:

FIGS. 6A-6D show images of setting up the optical element and stimulation device. FIG. 6A shows the leg of a subject with electrodes adhered and the optical element position marked. The position may be marked with a pen or other writing instrument comprising skin marking ink that is FDA approved, such as Genetian Violet Ink; prep resistant ink that can be used with aggressive skin prep such as for example CHG/isopropyl alcohol treatment; waterproof permanent ink; or ink that is easily removable such as with an alcohol. A pen can have a fine tip, an ultra-fine tip, or a broad tip. The pen may be sterile. As an alternative, the pen may be non-sterile. FIG. 6B shows the position of a rapid injector prior to inserting the probe. The probe may be inserted by hand or by a rapid injector. The rapid injector may provide for a quicker and less painful insertion process. FIG. 6C shows the probe and electrodes after insertion of the probe. A Velcro strap may be positioned around the area of interest to secure the optical element to the subject. Alternatively, the optical element may be held in place by any approach that maintains the stability of the apparatus. FIG. 6D shows a subject's leg with the optical element and stimulation device fully setup.

Figure 7:
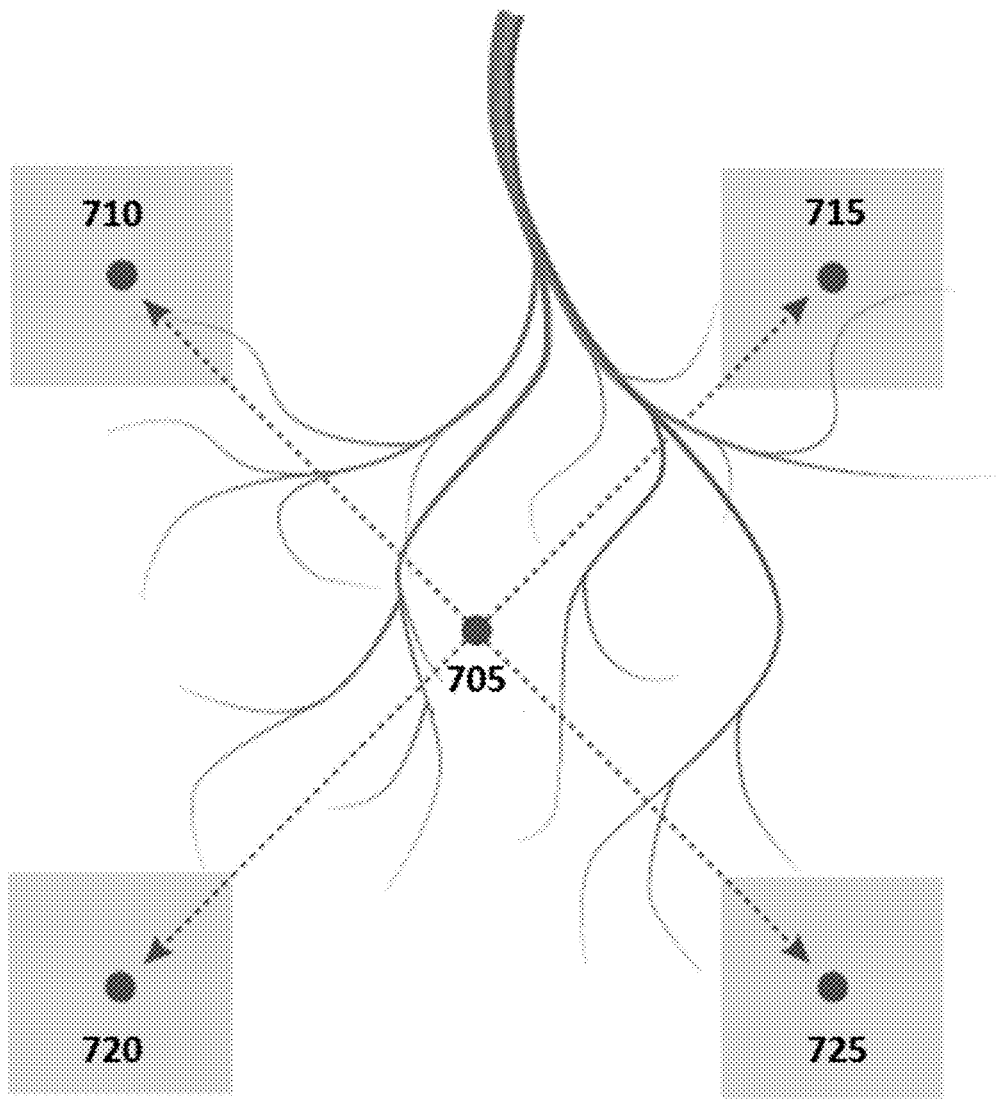
FIG. 7 is a schematic of the different current paths between anodes and the cathode of the optical element.

During stimulation of the muscle tissue, the probe may act as an electrode. The current may travel from the probe, through the tissue of the subject, to one or more of the electrodes adhered to the skin of the subject. Alternatively, the current may flow from one or more of the electrodes, through the tissue of the subject, to the probe. FIG. 7 shows example current paths for a stimulation device with four electrodes configured in a rectangle around the optical probe 705. Placement of multiple anodes may allow current to travel along different paths during muscle tissue stimulation. The different current paths may allow for access to different motor unit pools and recruitment of different motor units. The electrodes may be placed in proximal lateral position 710, proximal medial position 715, distal lateral position 720, distal medial position 725, or any combination thereof.

Figure 8B:
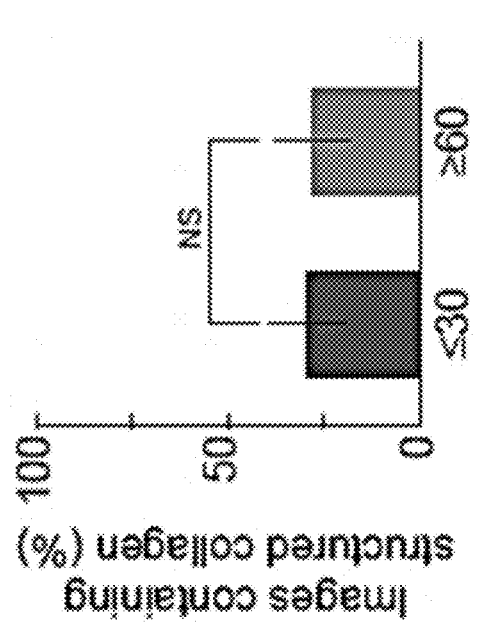
FIGS. 8A-8C show static images of muscle tissue and sarcomere and collagen data collected from the static images.
Figure 8B:
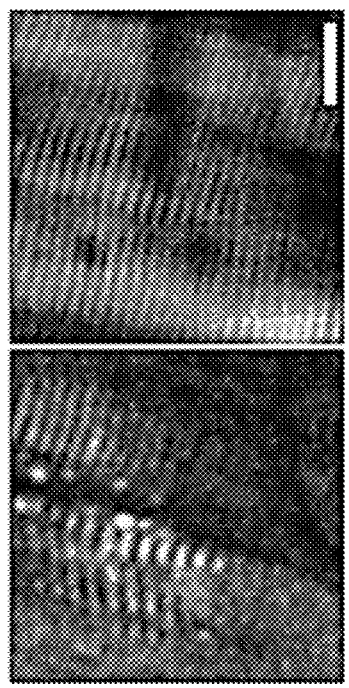
Figure 8A:
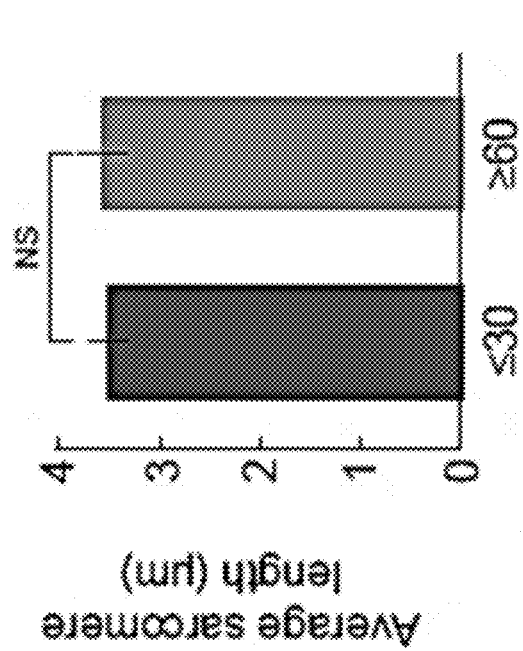
Figure 8A:
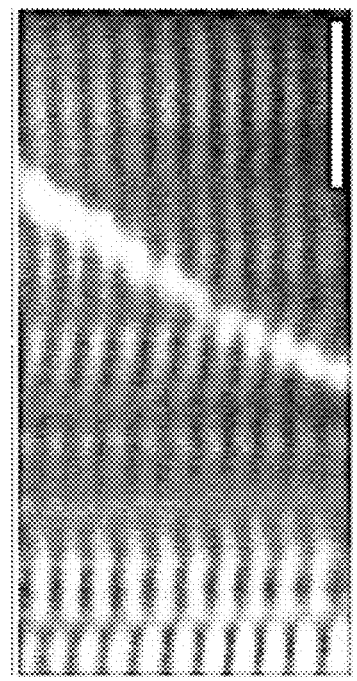
Figure 8C:
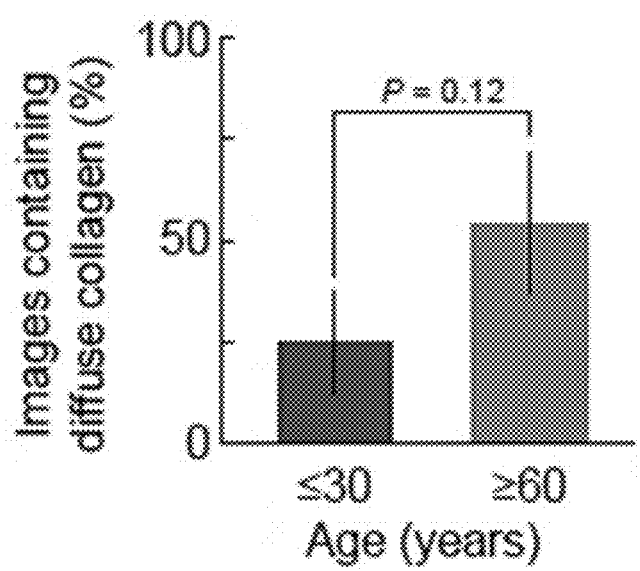
Figure 8C:
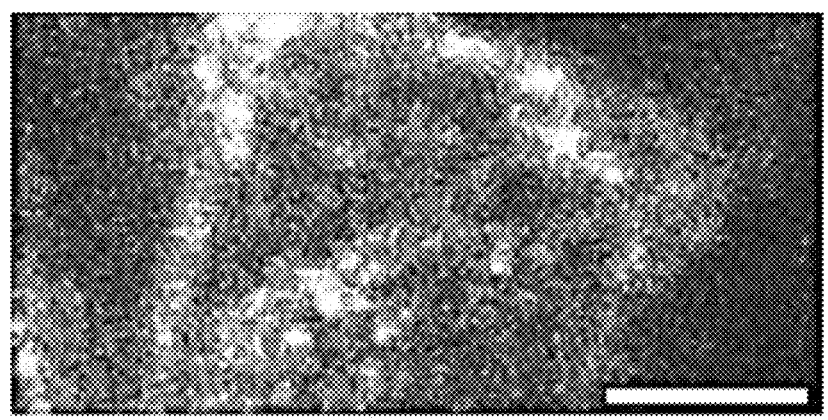

Two-dimensional images may be taken during static and dynamic imaging. Static imaging may include imaging of the muscle tissue without electrical stimulation. Dynamic imaging may include imaging during muscle tissue contraction and relaxation. Static images may be used to measure sarcomere length and collagen composition. FIG. 8A shows representative static images of short sarcomeres (right) and long sarcomeres (left) and corresponding sarcomere length data for subjects of different aged groups measured from the static images. The scale bar is 20 micrometers (μm). The subjects may include a young group (i.e., less than 30 years of age) and an elderly group (i.e., greater than 60 years of age). No difference is seen in sarcomere length between the young and elderly group. FIG. 8B shows the percent structured collagen measured during static imaging for two age groups and a representative image of a collagen bundle superimposed on sarcomere bands. The scale bar is 20 μm. No difference is seen in percent structured collagen between the young and elderly groups. FIG. 8C shows the percent unstructured collaged measured during static imaging for two age groups and a representative image of diffuse, unstructured collagen. The scale bar is 20 μm. A greater amount of unstructured collagen may be seen in the elderly group than in the young group.

The muscle tissue images may be generated in real-time. For example, the image is generated while the optical element transmits a beam of light from the light source towards the muscle tissue. The image may be generated at a frame rate of greater than or equal to about 1 frames per second (FPS), 2 FPS, 3 FPS, 4 FPS, 5 FPS, 10 FPS, or greater. Frame rate generally refers to the rate at which an imaging device displays consecutive images called frames. An image frame can provide a two-dimensional image of muscle tissue. The image frame may be a quadrilateral with any suitable dimensions. An image frame may be rectangular, in some cases with equal sides (e.g., square), for example, depicting a 200 μm by 200 μm two-dimensional image of the muscle tissue. The image frame may depict a two-dimensional of the muscle tissue having dimensions of about 50 μm by 50 μm, 100 μm by 100 μm, 150 μm by 150 μm, 200 μm by 200 μm, 250 μm by 250 μm, 300 μm by 300 μm, or greater. In some cases, the image frame may not have equal sides (e.g., rectangle)

Figure 9A:
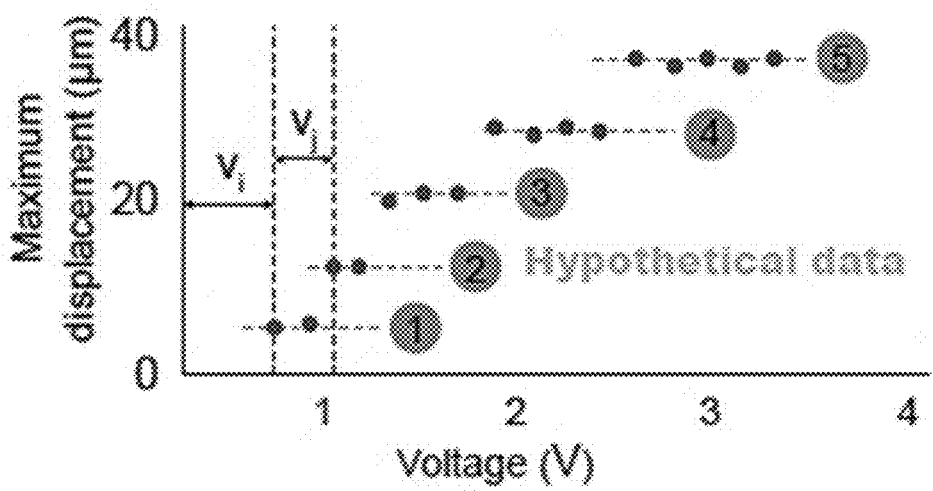
FIGS. 9A-9C shows hypothetical data of recruitment of motor units via electrical stimulation as a function of age.
Figure 9B:
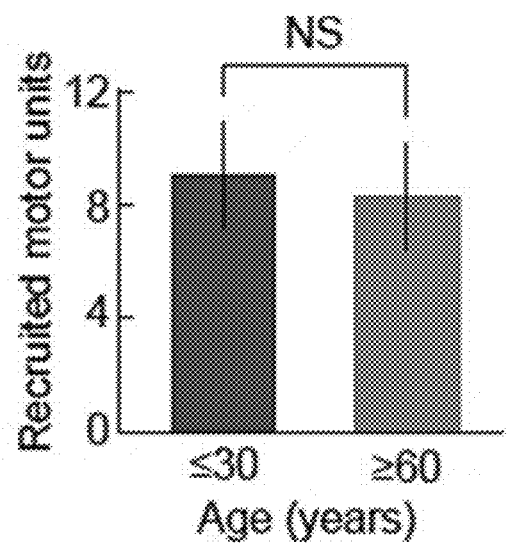
Figure 9C:
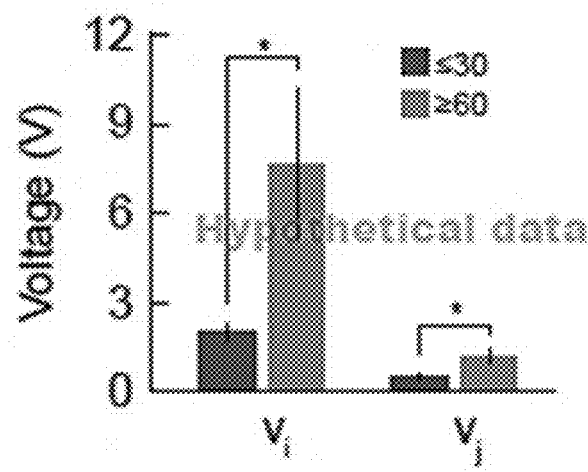

Dynamic imaging may be used to measure sarcomere displacement, motor unit recruitment, contraction and relaxation times, and contractility. During dynamic imaging, images may be taken as a function of time or as a function of voltage. For example, dynamic images may be taken at intervals that are greater than or equal to about 5 s, 4 s, 3 s, 2 s, 1 s, 500 ms, 250 ms, 100 ms, 50 ms, or less. Alternatively, dynamic images may be taken at intervals that are greater than or equal to about 2 V, 1.5 V, 1 V, 0.75 V, 0.5 V, 0.25 V, 0.1 V, or less. Recruitment of motor units via electrical stimulation may be age-dependent. Motor units may have a threshold electrical potential, or initiation voltage, to induce motor unit contraction. Successive electrical recruitment of motor units as electrical potential gradually increases may lead to step-wise jumps in sarcomere displacement. Each step-wise jump may indicate the recruitment of an additional motor unit. FIG. 9A shows a hypothetical data set of maximum sarcomere displacement and motor unit recruitment as a function of voltage. The data set includes five representative motor units and shows the initiation voltage, the voltage to recruit the first motor unit, and the jump voltage, the voltage difference between recruitment of the first and second motor units. FIG. 9B shows the average number of motor units recruited for young subjects and elderly subjects. FIG. 9C shows hypothetical data of the average initiation and jump voltage for young and elderly subjects.

Figure 10A:
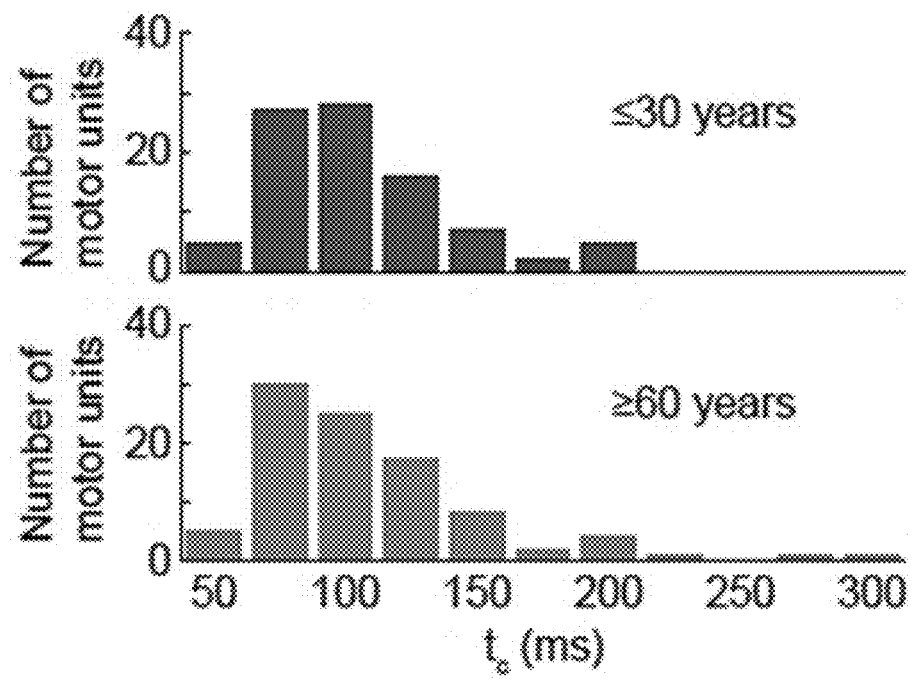
FIGS. 10A and 10B show contractility dynamics of different aged subjects.
Figure 10B:
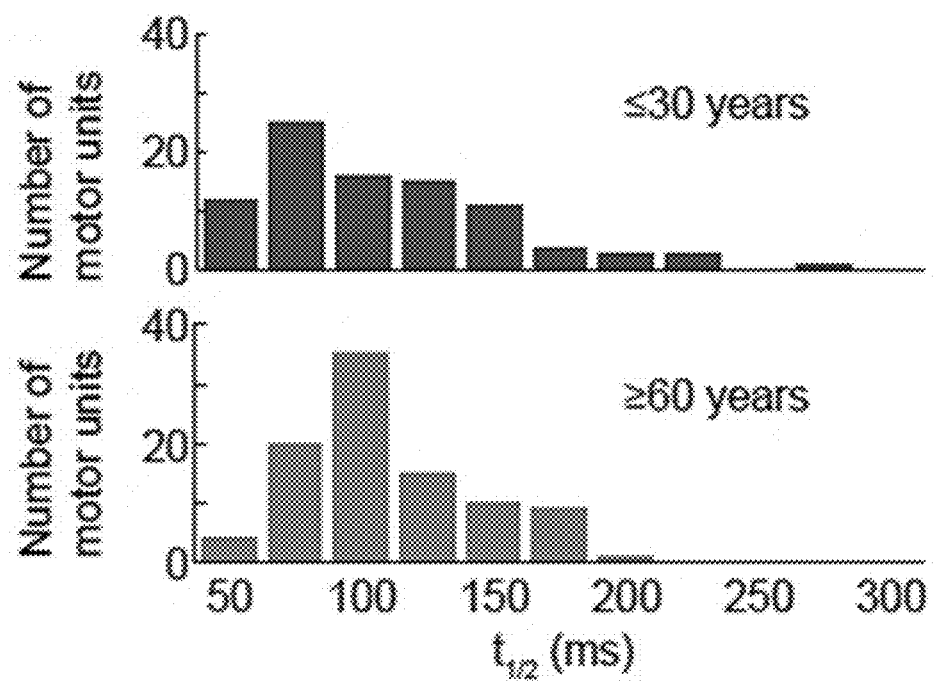
Figure 11A:
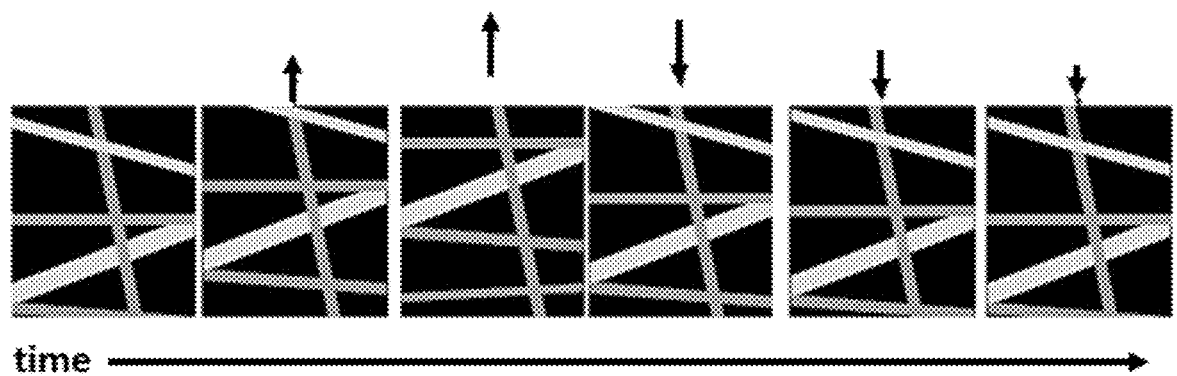
Figure 11B:
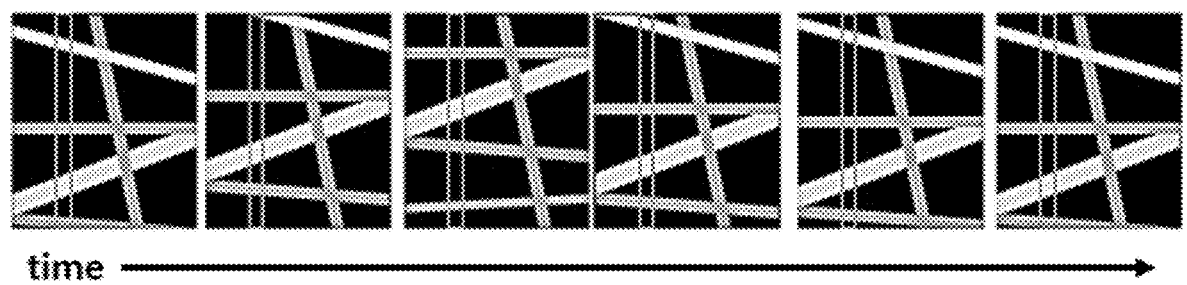

Contractility dynamics may be measured during dynamic imaging. Contractility dynamics may be altered as people age. FIG. 10A shows representative rise time distribution of motor units for young and elderly subjects. Rise time distributions may be taken while stimulation voltage is increased. FIG. 10B shows representative half relaxation time dynamics of motor units for young and elderly subjects. Contractility dynamics may be measured by dynamic imaging or by dynamic line scanning. FIG. 11A shows a series of two-dimensional images taken over a period of time during dynamic imaging. Each rectangle represents the field of view of the microscope. During electrical stimulation, off-screen motor units may pull the field of view (FOV) up and, as the motor units relax, the FOV may return back to baseline. To increase imaging efficiency, a line scan may be performed rather than a two-dimensional scan. FIG. 11B shows the line scan area taken from the representative series of images from FIG. 11A. FIG. 11C shows the representative line scans without the surrounding two-dimensional image. The line scans may be assembled into a single image to show vertical displacement of the sarcomeres. FIG. 11D shows the assembled line scan images from FIG. 11C. FIG. 11D shows the assembled line scan images with a representative curve fit to the sarcomere displacement. FIG. 11F shows the extracted displacement versus time curve that may be used to assess contractility and contraction and relaxation dynamics.

To generate a two-dimensional image or line scan, signals from a plurality of focal planes can be collected. The plurality of different focal planes can be obtained by changing a relative position of a mobile lens with respect to the muscle tissue. The mobile lens may be in optical communication with the probe. Changing the relative position of the mobile lens may comprise translating the mobile lens. The mobile lens can be translated at a cyclic rate to produce a frame rate of greater than or equal to about 2 frames per second (FPS), 3 FPS, 4 FPS, 5 FPS, 10 FPS, or greater. The cyclic rate may be greater than or equal to 1 Hz, 2 Hz, 3 Hz, 4 Hz, 5 Hz or greater. As an alternative or in conjunction with a mobile lens, the plurality of different focal planes can be obtained by modulating a curvature of an electrically or electro-mechanically tunable lens that is in electrical or electro-mechanical communication with the optical probe. Tunable lenses can refer to optical elements whose optical characteristics, such as focal length and/or location of the optical axis, can be adjusted during use, for example by electronic control. Electrically-tunable lenses may contain a thin layer of a suitable electro-optical material (e.g., a material whose local effective index of refraction, or refractive index, changes as a function of the voltage applied across the material). An electrode or array of electrodes can be used to apply voltages to locally adjust the refractive index to a usable value. The electro-optical material may comprise liquid crystals. Voltage can be applied to modulate the axis of birefringence and the effective refractive index of an electro-optical material comprising liquid crystals. In some cases, polymer gels can be used. A tunable lens may comprise an electrode array that defines a grid of pixels in the liquid crystal, similar to pixel grids used in liquid-crystal displays. The refractive indices of the individual pixels may be electrically controlled to give a desired phase modulation profile, phase modulation profile referring to the distribution of the local phase shifts that are applied to light passing through the layer as the result of the locally-variable effective refractive index over the area of the electro-optical layer of the tunable lens. Alternatively, or in addition to, a two-dimensional image may be created by combining a plurality of successive line scans into an image demonstrating the time course over a certain time interval. This time interval can produce a frame rate of greater than or equal to about 1 frames per second (FPS), 2 FPS, 3 FPS, 4 FPS, 5 FPS, 6 FPS, 8 FPS, 10 FPS, or greater.

Figure 12A:
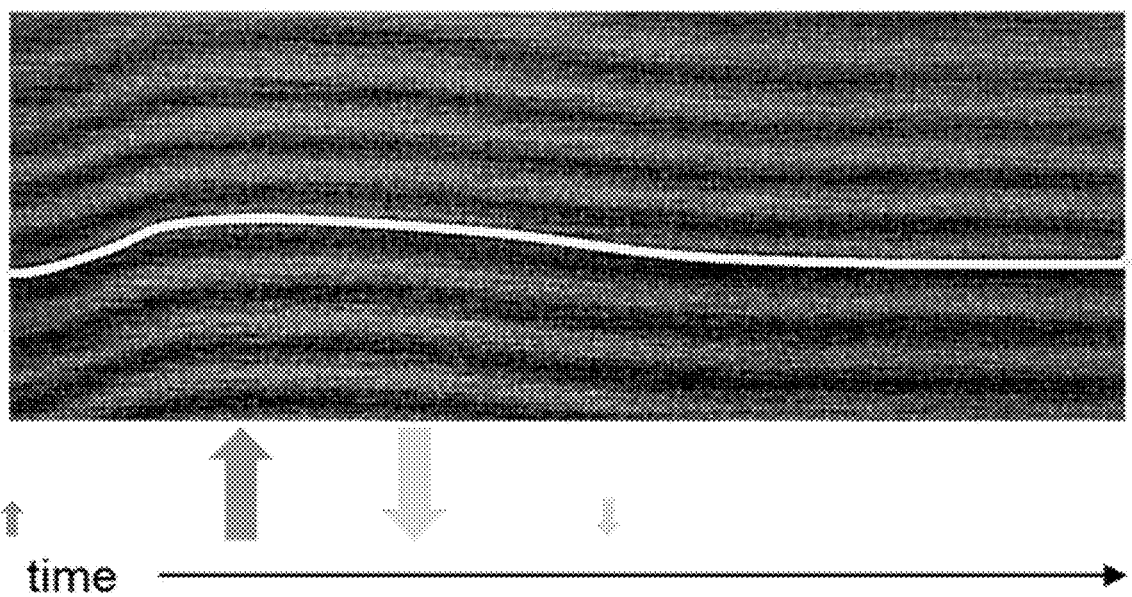
FIG. 12A shows a representative image of motor unit recruitment during electrical stimulation.
Figure 12B:
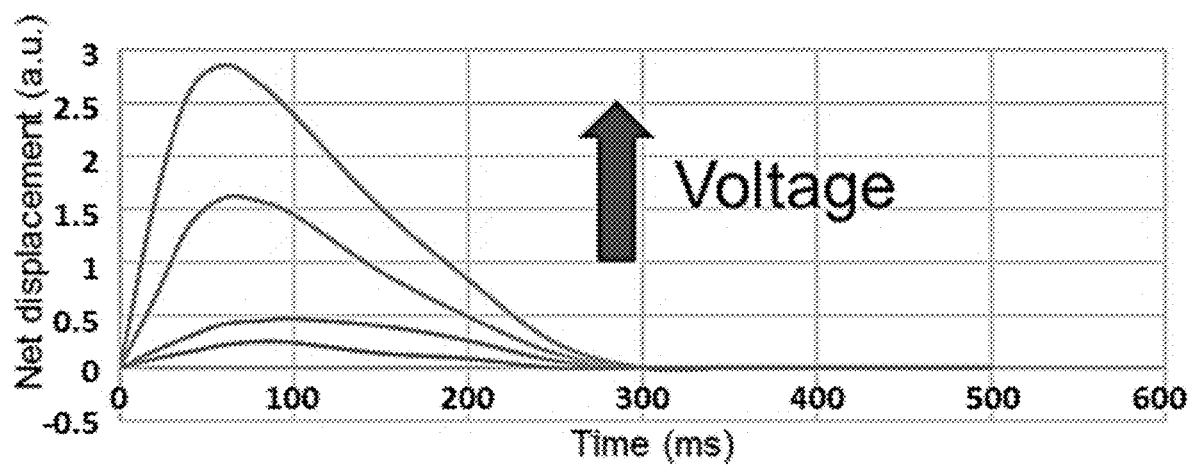
FIG. 12B shows the net tissue displacement as a function of time for a range of stimulation voltages that recruit additional motor units.
Figure 13A:
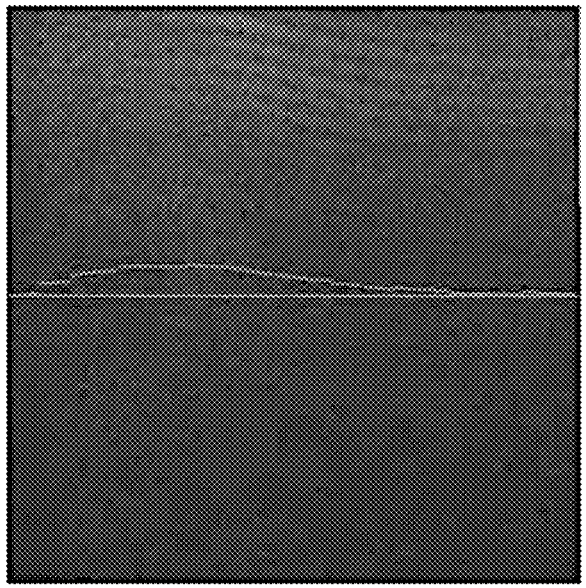
FIGS. 13A-13D show representative traces for four different electrical stimulation current paths.
Figure 13B:
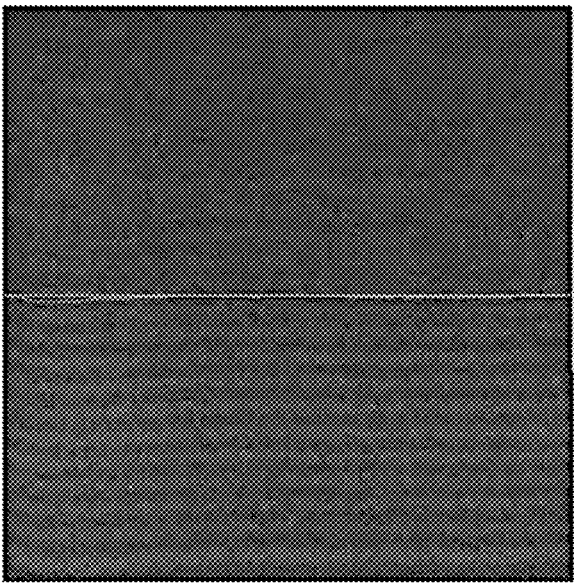
Figure 13C:
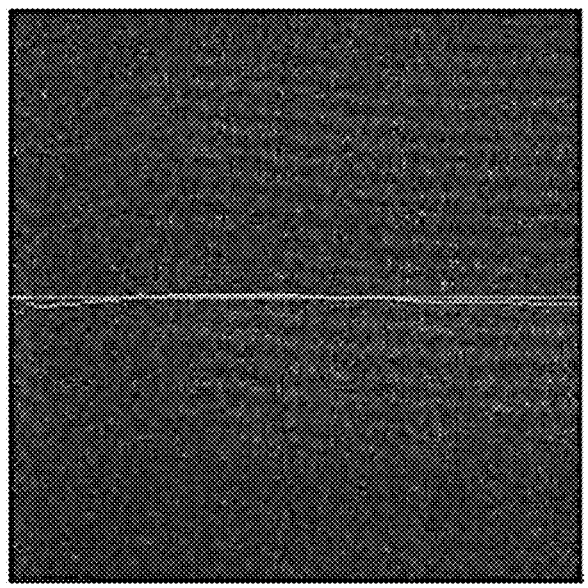
Figure 13D:
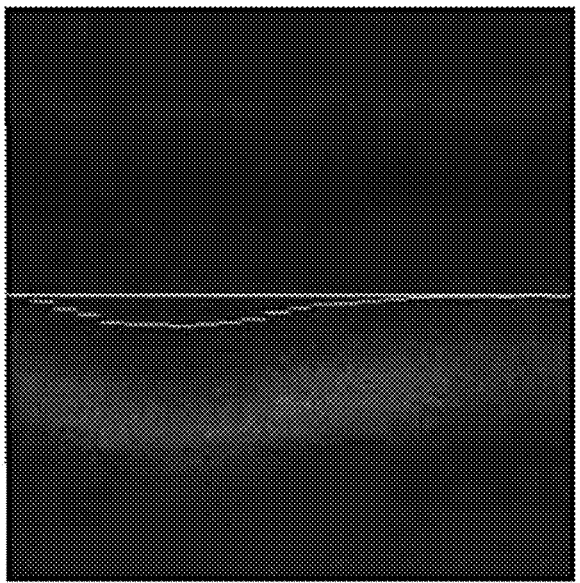

FIG. 12A shows a representative two-dimensional image of motor unit recruitment and shift in FOV. During stimulation, motor units outside the FOV may pull motor units up to create a non-linear profile. Once stimulation has halted, the motor units may relax and return to the baseline profile. FIG. 12B is a representative figure showing increasing voltage increasing sarcomere displacement as a function of time. After stimulation has halted, the net displacement may return back to the baseline (e.g., zero displacement). FIGS. 13A-13D show representative traces and FOV shift during electrical stimulation from different current paths. The electrodes may be placed as shown in FIG. 7. FIG. 13A shows a representative trace for electrical stimulation with a distal lateral anode. FIG. 13B shows a representative trace for electrical stimulation with a proximal lateral anode. FIG. 13C shows a representative trace for electrical stimulation with a distal medial anode. FIG. 13D shows a representative trace for electrical stimulation with a proximal medial anode.

Figure 14:
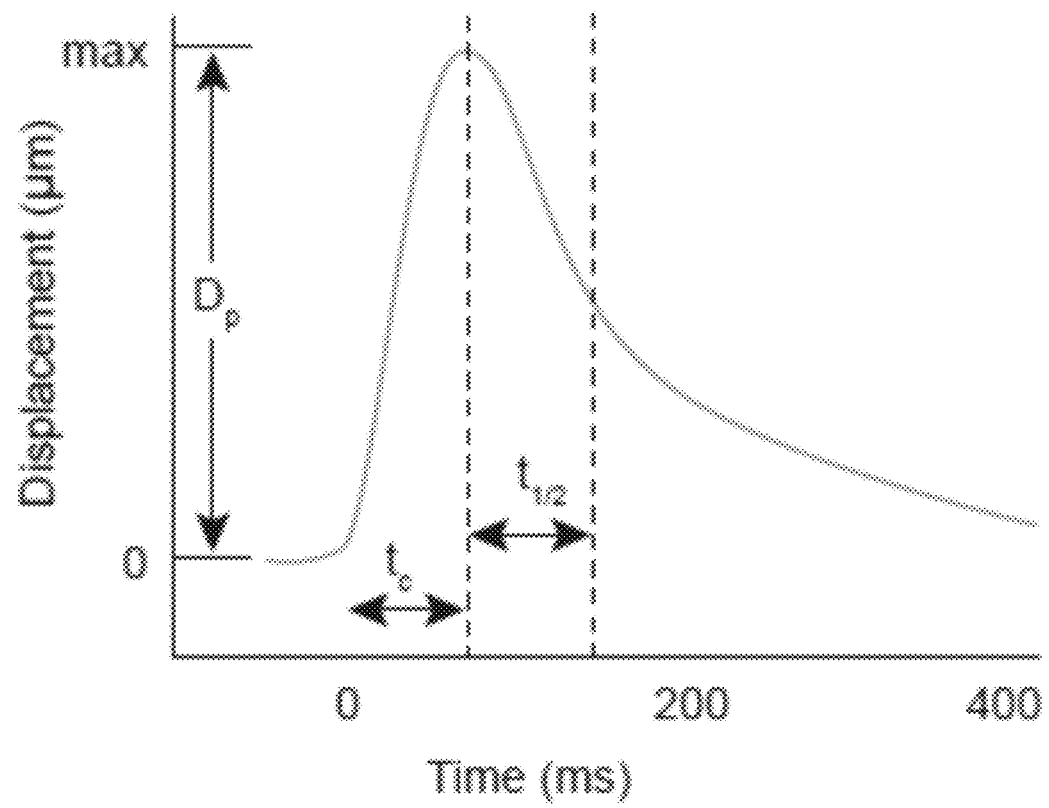
FIG. 14 shows a schematic of muscle twitch as a function of time during electrical stimulation.

FIG. 14 shows an example displacement figure that may be generated from dynamic two-dimensional and dynamic line scan imaging. The displacement curve may be used to determine maximum sarcomere displacement, the rise time, and the half relaxation time. The half relaxation time may be defined as the time from maximum displacement to half the magnitude of the maximum displacement.

Computer Systems

Figure 21:
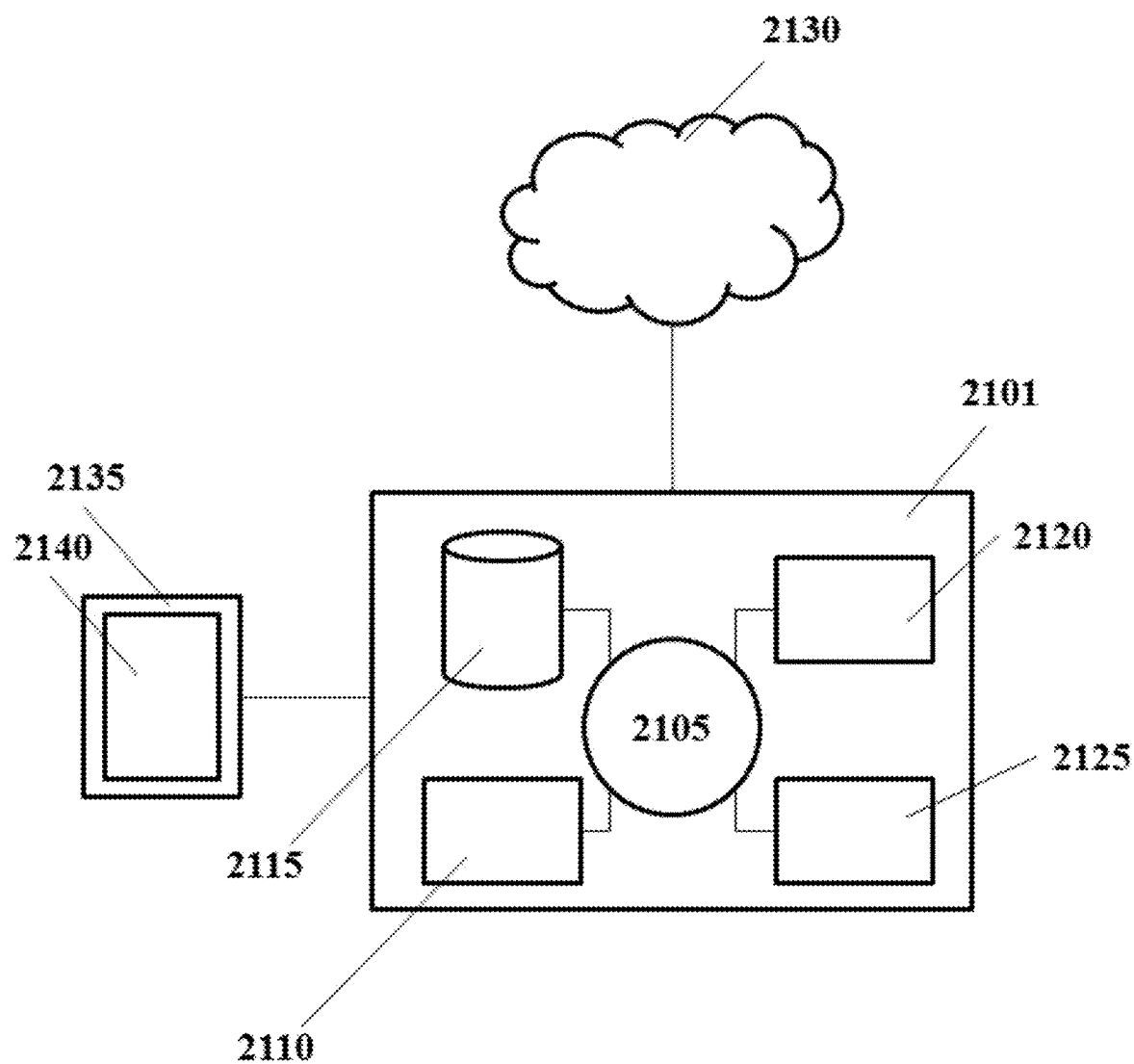
FIG. 21 shows an example schematic of a computer control system that is programmed or otherwise configured to implement methods provided herein.

The present disclosure provides computer control systems that are programmed to implement methods of the disclosure. FIG. 21 shows a computer system 2101 that can be programmed or otherwise configured to implement the methods provided herein. The computer system 2101 can regulate various aspects of identifying a muscle tissue disease of a subject, such as, for example, collecting at least a subset of the signals generated during muscle tissue stimulation to generate images of the muscle tissue and characterize tissue length and displacement. The computer system 2101 can be an electronic device of a user or a computer system that can be remotely located with respect to the electronic device. The electronic device can be a mobile electronic device.

The computer system 2101 includes a central processing unit (CPU, also "processor" and "computer processor" herein) 2105, which can be a single core or multi core processor, or a plurality of processors for parallel processing. The computer system 2101 also includes memory or memory location 2110 (e.g., random-access memory, read-only memory, flash memory), electronic storage unit 2115 (e.g., hard disk), communication interface 2120 (e.g., network adapter) for communicating with one or more other systems, and peripheral devices 2125, such as cache, other memory, data storage and/or electronic display adapters. The memory 2110, storage unit 2115, interface 2120 and peripheral devices 2125 are in communication with the CPU 2105 through a communication bus (solid lines), such as a motherboard. The storage unit 2115 can be a data storage unit (or data repository) for storing data. The computer system 2101 can be operatively coupled to a computer network ("network") 2130 with the aid of the communication interface 2120. The network 2130 can be the Internet, an internet and/or extranet, or an intranet and/or extranet that can be in communication with the Internet. The network 2130 in some cases can be a telecommunication and/or data network. The network 2130 can include one or more computer servers, which can enable distributed computing, such as cloud computing. The network 2130, in some cases with the aid of the computer system 2101, can implement a peer-to-peer network, which may enable devices coupled to the computer system 2101 to behave as a client or a server.

The CPU 2105 can execute a sequence of machine-readable instructions, which can be embodied in a program or software. The instructions may be stored in a memory location, such as the memory 2110. The instructions can be directed to the CPU 2105, which can subsequently program or otherwise configure the CPU 2105 to implement methods of the present disclosure. Examples of operations performed by the CPU 2105 can include fetch, decode, execute, and writeback.

The CPU 2105 can be part of a circuit, such as an integrated circuit. One or more other components of the system 2101 can be included in the circuit. In some cases, the circuit is an application specific integrated circuit (ASIC).

The storage unit 2115 can store files, such as drivers, libraries and saved programs. The storage unit 2115 can store user data, e.g., user preferences and user programs. The computer system 2101 in some cases can include one or more additional data storage units that are external to the computer system 2101, such as located on a remote server that is in communication with the computer system 2101 through an intranet or the Internet.

The computer system 2101 can communicate with one or more remote computer systems through the network 2130.

For instance, the computer system 2101 can communicate with a remote computer system of a user (e.g., service provider). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 2101 via the network 2130.

Methods as described herein can be implemented by way of machine (e.g., computer processor) executable code stored on an electronic storage location of the computer system 2101, such as, for example, on the memory 2110 or electronic storage unit 2115. The machine executable or machine readable code can be provided in the form of software. During use, the code can be executed by the processor 2105. In some cases, the code can be retrieved from the storage unit 2115 and stored on the memory 2110 for ready access by the processor 2105. In some situations, the electronic storage unit 2115 can be precluded, and machine-executable instructions are stored on memory 2110.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 2101, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 2101 can include or be in communication with an electronic display 2135 that comprises a user interface (UI) 2140 for providing, for example, an image of a muscle tissue. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 2105. The algorithm can, for example, generate an image using the subset of signals collected at during muscle tissue stimulation. In some cases, the algorithm can generate a depth profile in real-time.

EXAMPLE 1

Muscle Imaging in Young and Elderly Subjects

Muscle imaging is performed with ten volunteers aged eighteen to twenty-nine and twelve volunteers aged sixty-two to seventy-five. Subjects do not have major lower limb disabilities or metastatic cancer and are not currently taking medications that may influence muscle function. The body mass index (BMI) for all subjects is less than 30, which may ensure that optical element can reach the vastus lateralis and is not imaging subcutaneous fat. Subjects report no recent history with needle-induced syncope. The study protocol is approved by Salus Institutional Review Board in accordance with FDA guidelines (21 C.F.R. 50).

The subjects are divided into four groups: young males, young females, elderly males, and elderly females. Subjects in the young groups are under thirty years of age and subjects in the elderly group are over sixty years of age. The physical characteristics of the subjects are measured, including mass, body fat percentage, and muscle percentage. Table 1 summarizes the physical characteristics of the four groups. Physical strength parameters, including hand grip strength, walking speed, and knee torque, are measured as well.

Table 1. Average Physical Characteristics for the Four Groups.

TABLE 1

| | Average physical characteristics for the four groups. | | | |
|---|---|---|---|---|
| | Young-Males (N = 5) | Young-Females (N = 5) | Elderly-Males (N = 6) | Elderly-Females (N = 4) |
| Age (year) | 23.5 (3.9) | 27.1 (3.4) | 67.5 (4.4)* | 68.8 (2.6)* |
| BMI (kg/m$^2$) | 25.2 (2.8) | 21.7 (1.7) | 26.4 (2.0) | 26.6 (3.1)* |
| Body fat % | 16.5 (5.8) | 20.5 (4.2) | 22.9 (4.6)$^{p\ =\ 0.07}$ | 34.9 (5.2)* |
| Muscle % | 46.5 (3.1) | 36 (2.5) | 29.0 (2.9)* | 25.0 (0)* |

To image and characterize the muscle tissue of the subjects, each subject is injected with the probe, anode electrodes are placed, and the microscope is positioned. The injection and electrode locations may be marked prior to injection of the probe to minimize the amount of time the probe is in the muscle tissue. The injection location may be marked on the leg using a guide that is positioned using the distal boundary of the vastus lateralis, which may be found by palpation. Prior to injecting the optical element, the skin may be anesthetized with a 4% lidocaine cream. To increase electrical contact, the skin may be shaved directly under the electrode pads. The skin may also be cleaned with alcohol swabs and gently abraded without removing the skin markings. The electrodes (Syrtenty, TSR-S2020-16, cut to 1 inch by 1 inch squares) are placed on dry skin and the electrode wires are attached. The optical element may be injected with a rapid injector after cleaning the skin with an alcohol swab. The microscope is attached to the probe after injection and a Velcro strap may be used to secure the microscope to the leg. In this example, muscle tissue is stimulated with single 100 μs pulses of electrical potential.

Figure 15A:
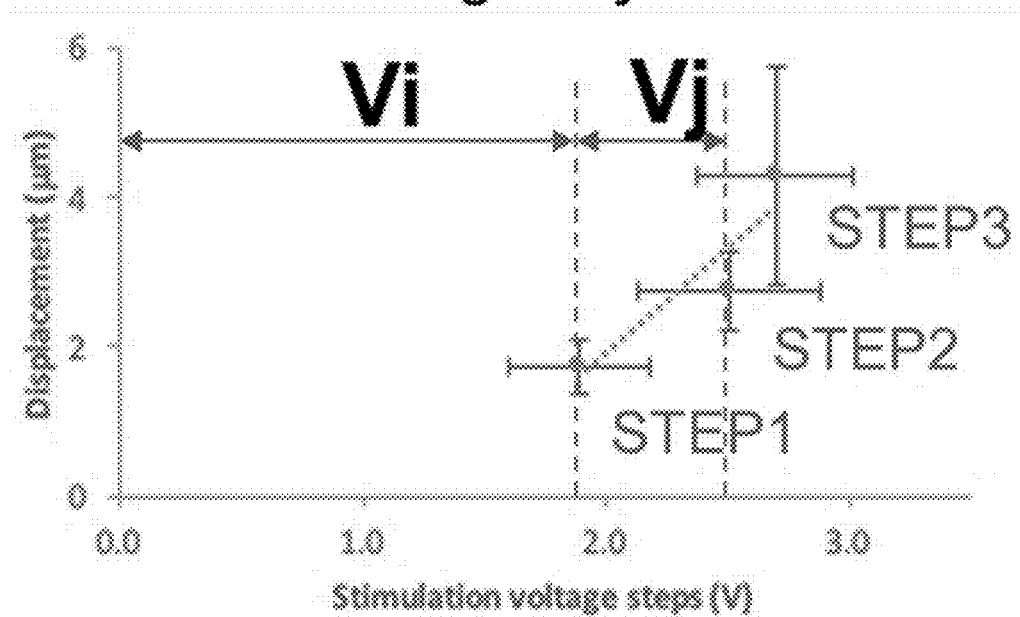
FIGS. 15A-15C show initiation voltages and jump voltages for different aged subjects.

FIG. 15A shows the average sarcomere displacement as a function of voltage for the young subject group. The muscle tissue is electrically stimulated with zero volts to approximately 3 V. Sarcomere displacement ranges from approximately 2 μm for a recruitment of a single motor unit to approximately 4 μm for recruitment of three motor units.

Figure 15B:
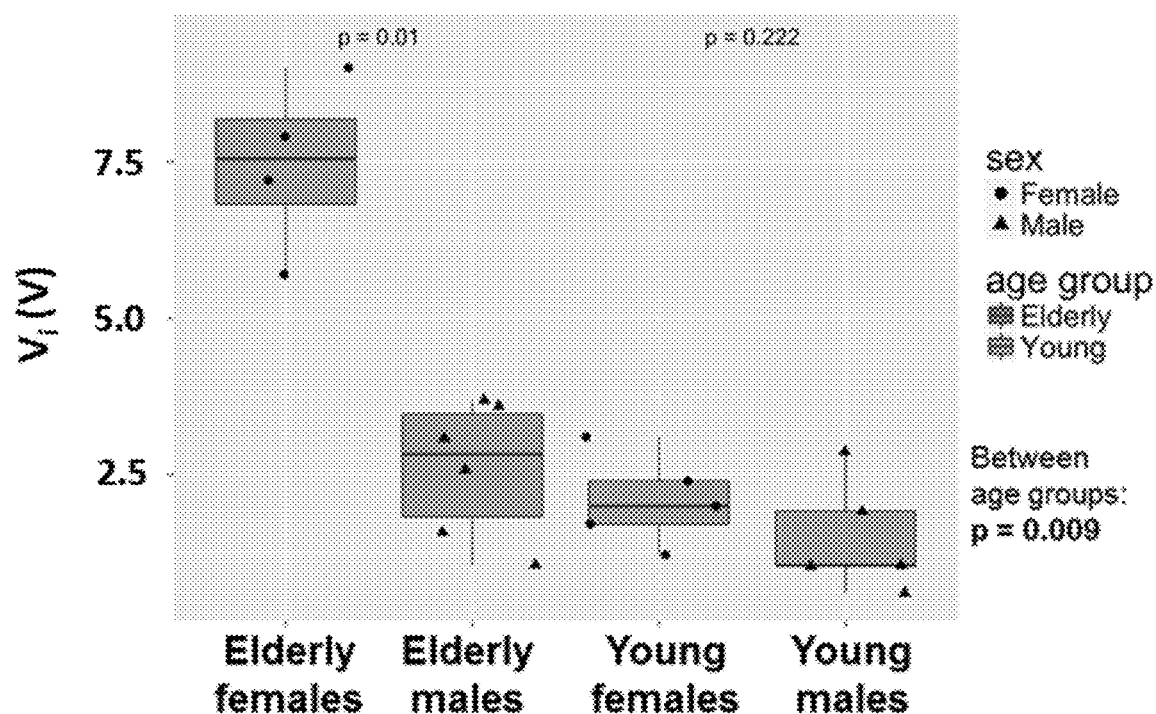
Figure 15C:
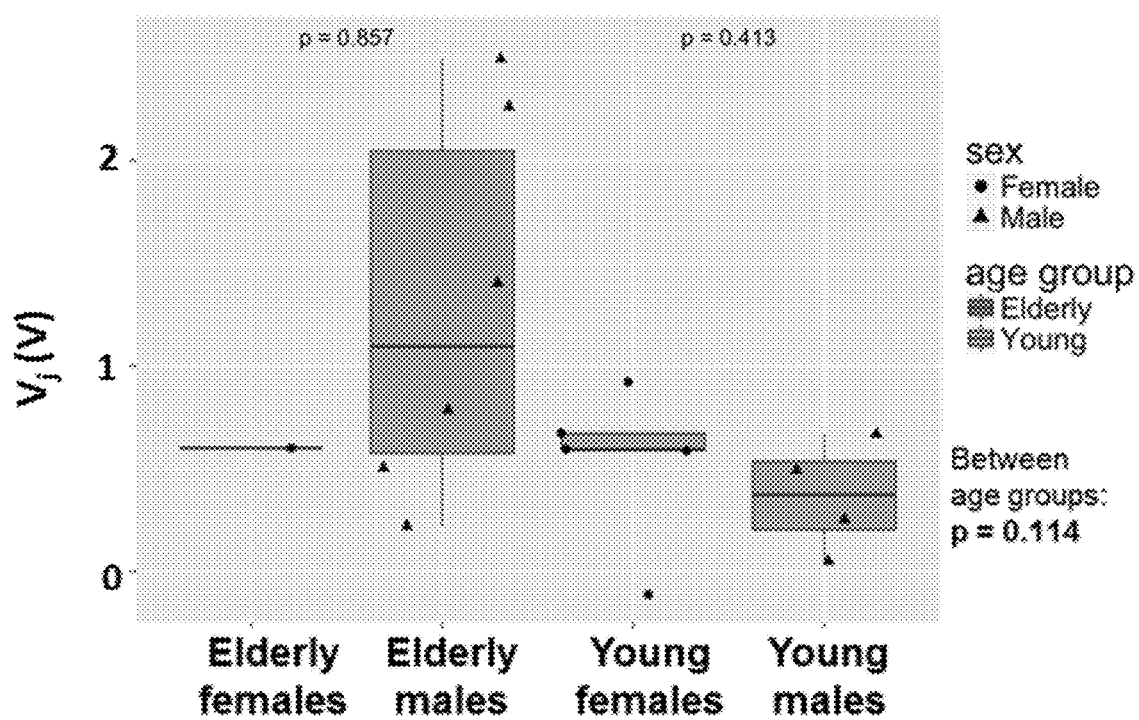

FIGS. 15B and 15C show the initiation and jump voltage, respectively, for the four subject groups. Elderly females show the largest initiation voltage and elderly males, young females, and young males show initiation voltages that are not statistically different. The jump voltage for all four groups is statistically similar.

Figure 16A:
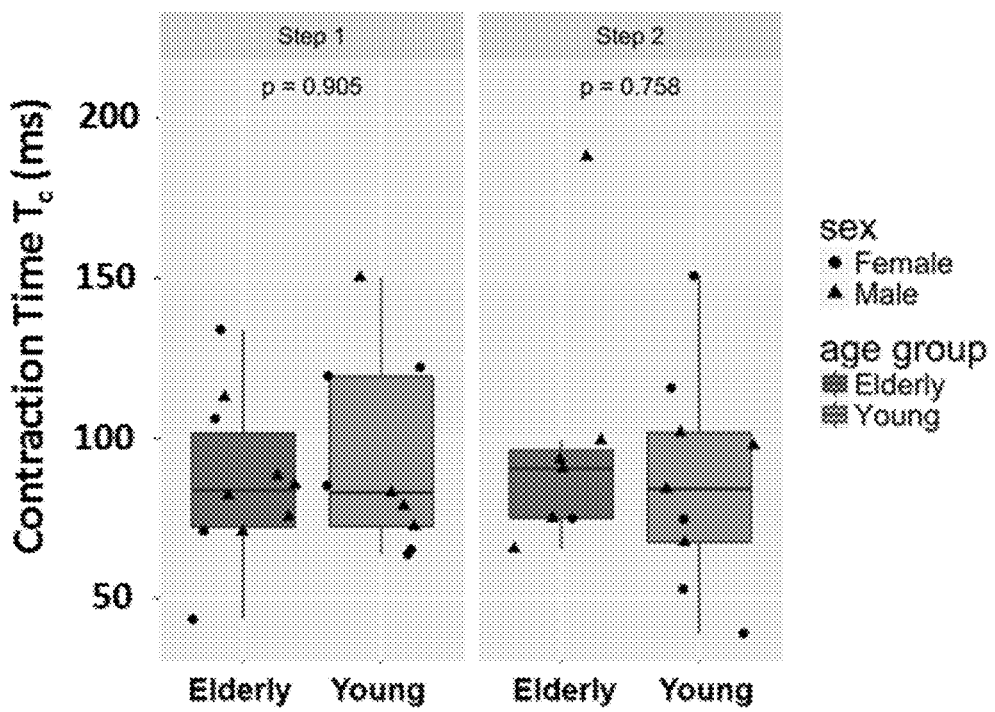
FIGS. 16A and 16B show the average contraction and relaxation times for a variety of subjects.
Figure 16B:
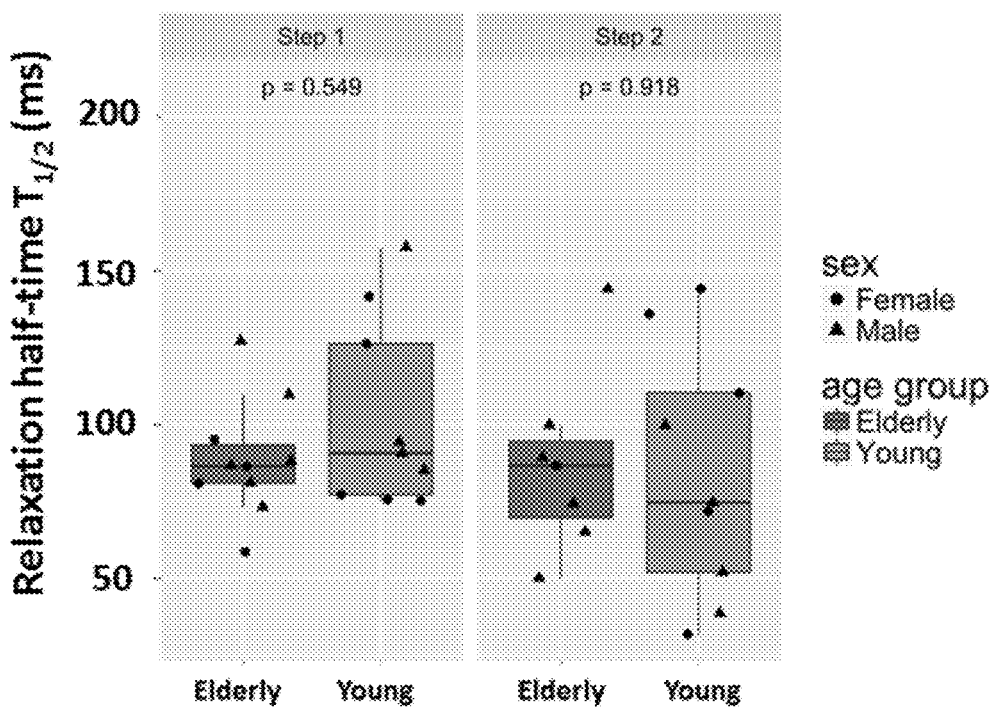
Figure 17:
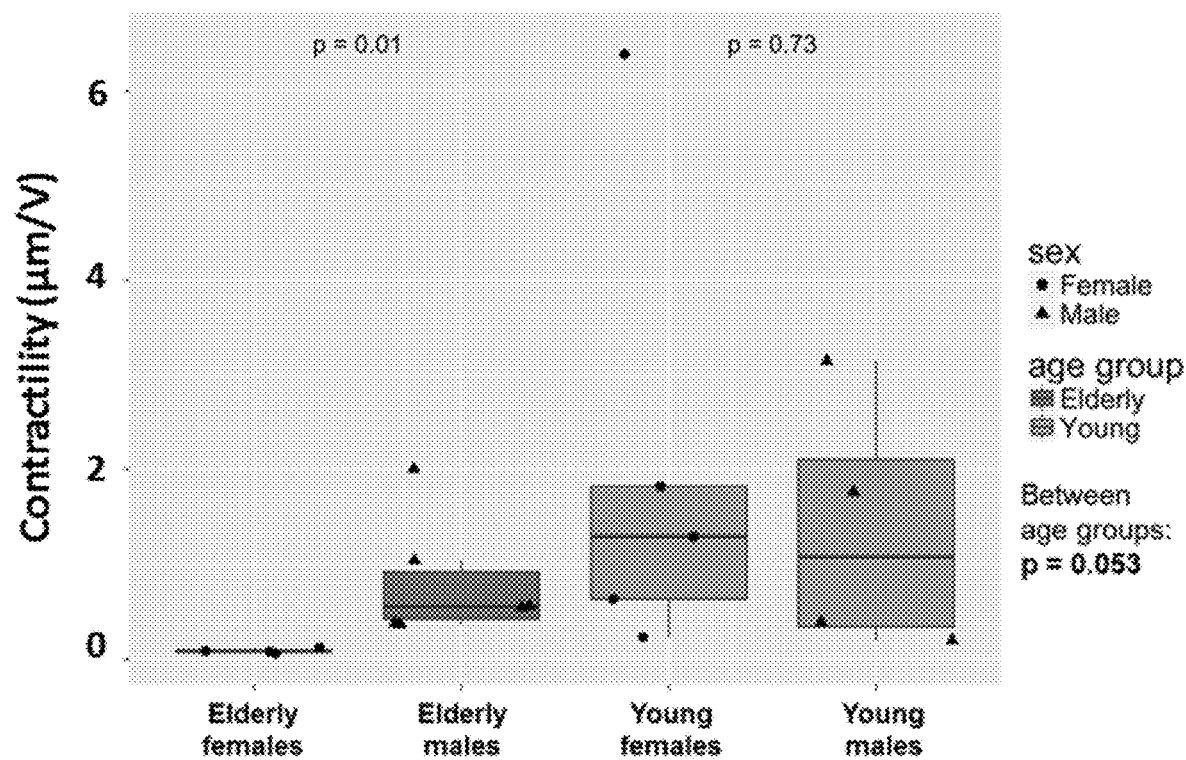
FIG. 17 shows the average contractility of for young, elderly, male, and female subjects.

FIGS. 16A and 16B show the contraction time and relaxation half time for the four subject groups. No statistical difference is seen between the subject groups for contraction time and relaxation half time. FIG. 17 shows the contractility of the four subject groups. A small decrease in contractility may be seen in the elderly groups as compared to the young groups.

Figure 18A:
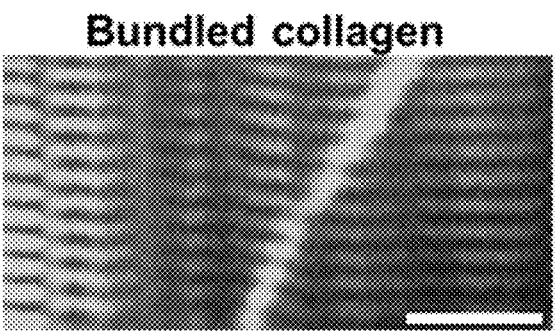
FIGS. 18A-18D show bundled and unstructured collagen characteristics for different aged subjects.
Figure 18B:
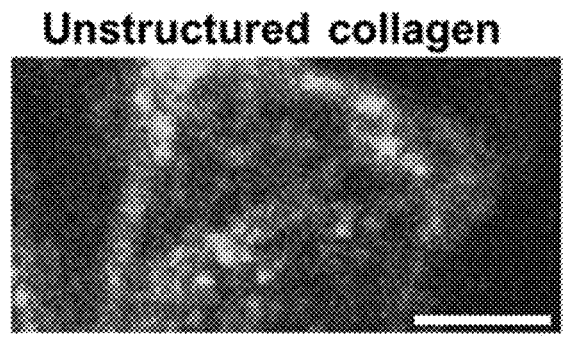
Figure 18C:
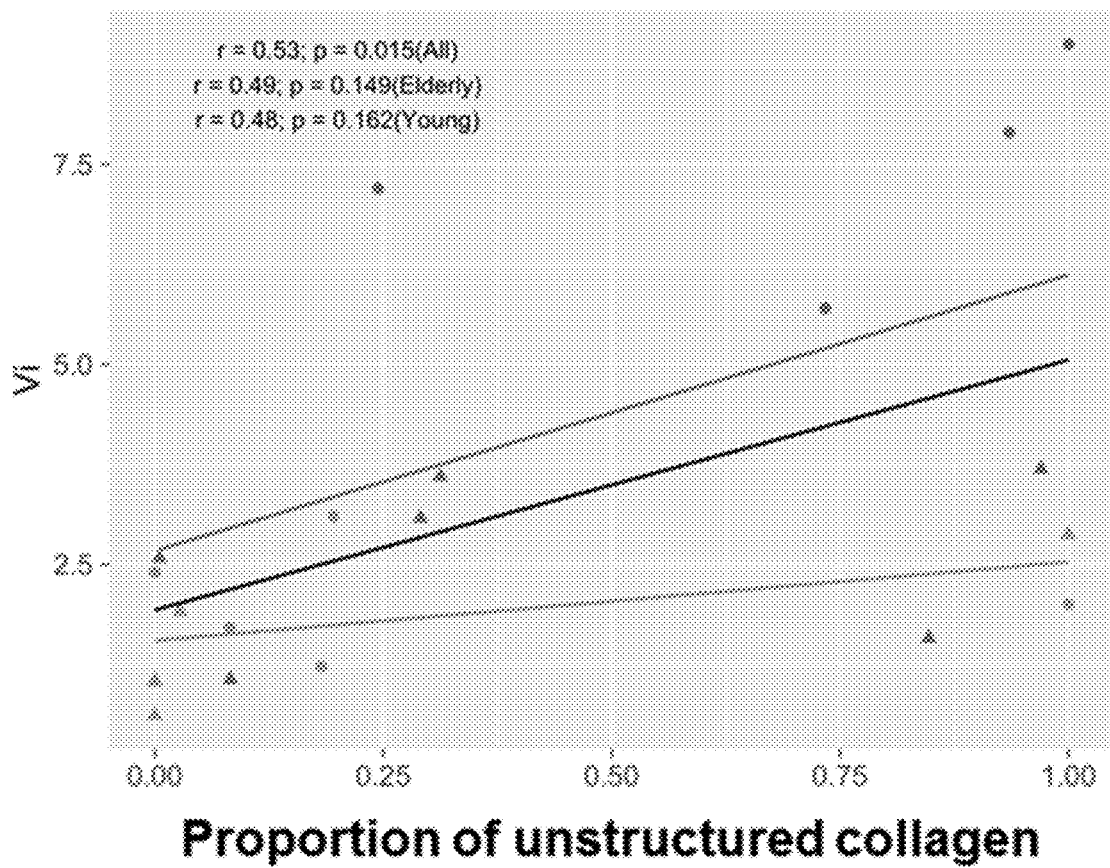
Figure 18D:
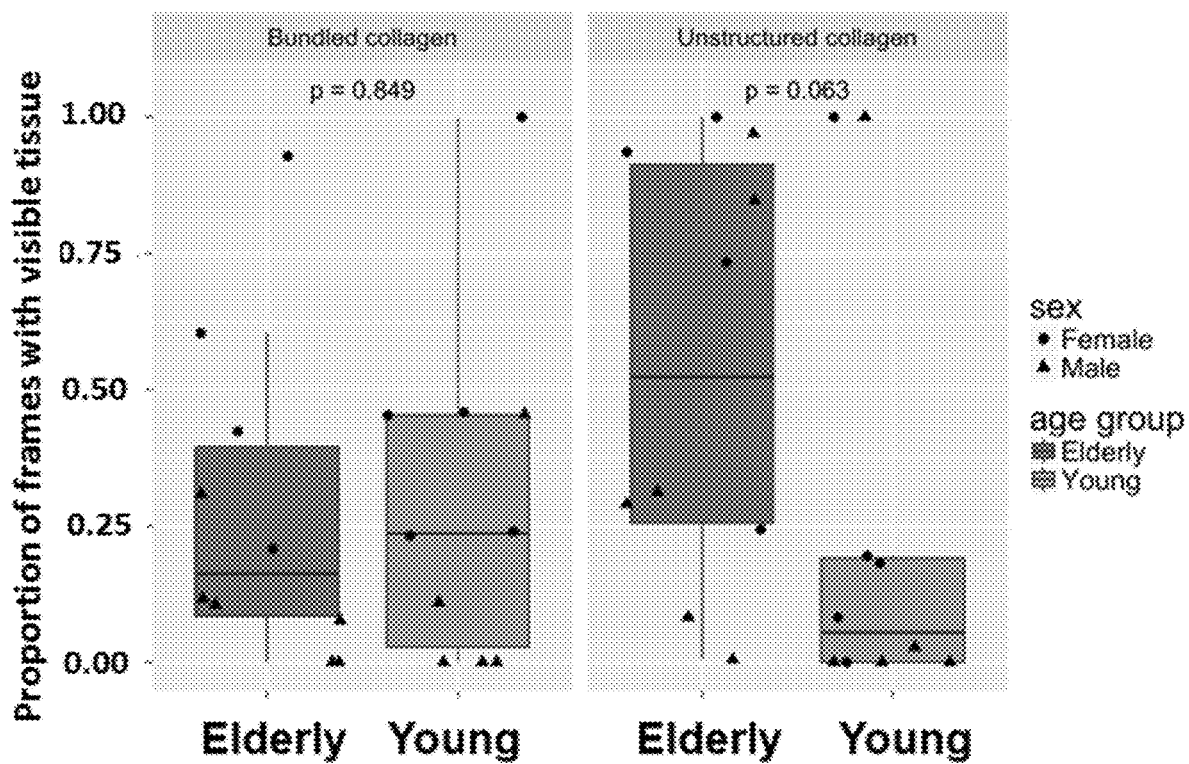

FIGS. 18A and 18B are representative images of bundled or structured and unstructured collagen. FIG. 18C shows the initiation voltage as a function of unstructured collagen for the four subject groups. As the proportion of unstructured collagen increases the initiation voltage may also be seen to increase. FIG. 18D shows the proportion of the FOV with visible tissue for the four subject groups.

Figure 19A:
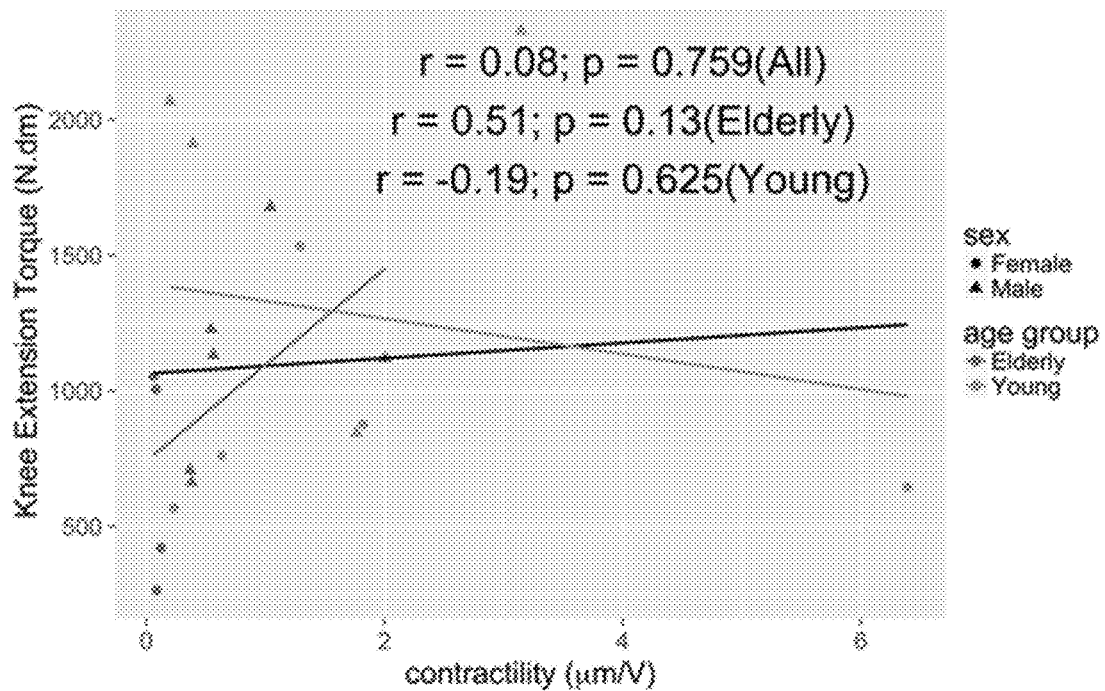
FIGS. 19A-19C show physical performance measurements as a function of contractility for different aged subjects.
Figure 19B:
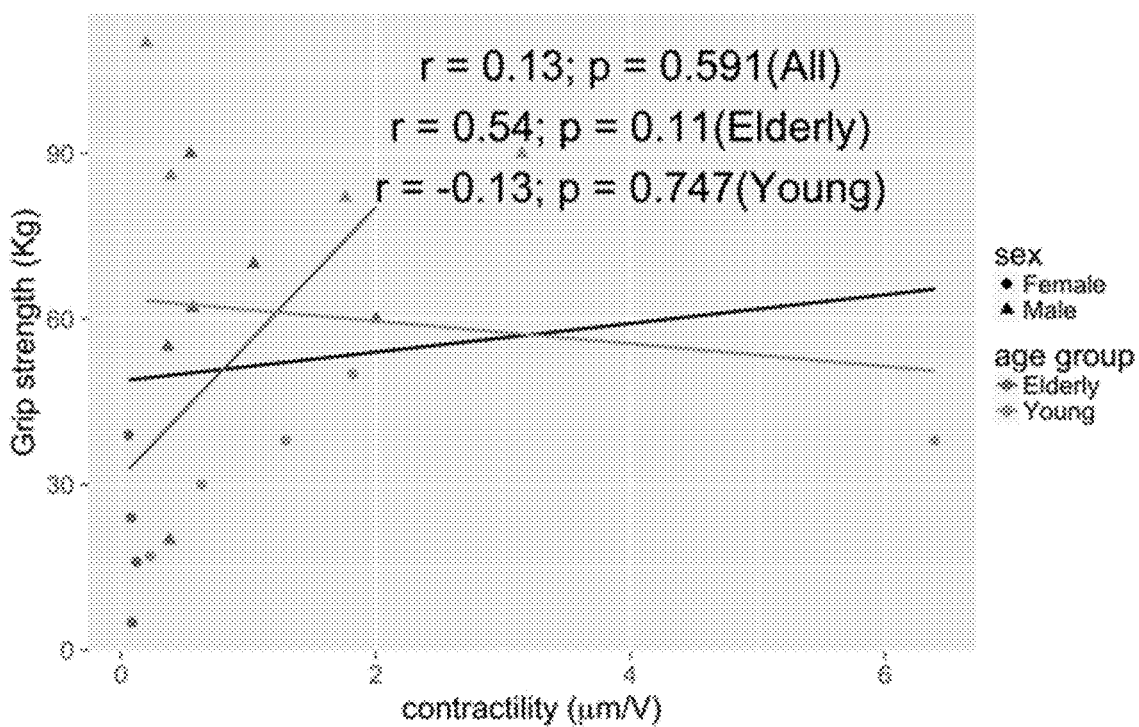
Figure 19C:
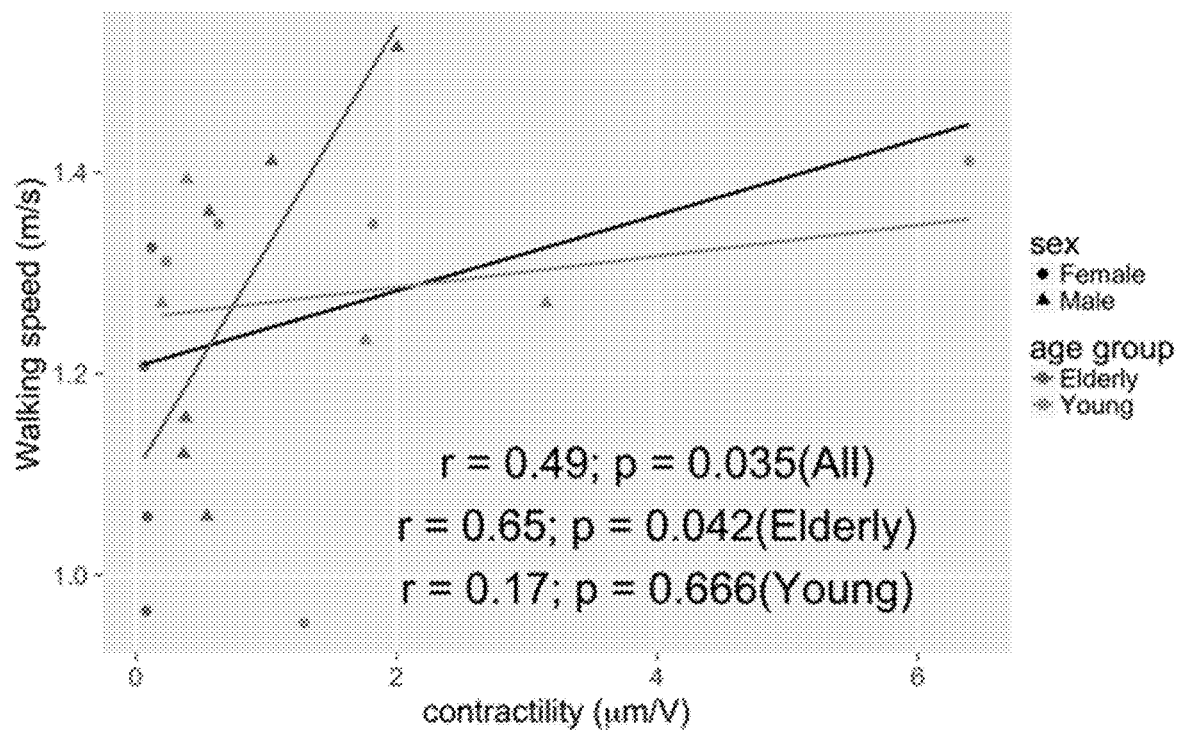

FIGS. 19A-19C show the physical strength measurements as a function of contractility for the four subject groups. FIG. 19A shows knee extension torque as a function of contractility. FIG. 19B shows grip strength as a function of contractility. FIG. 19C shows walking speed as a function of contractility.

Figure 20:
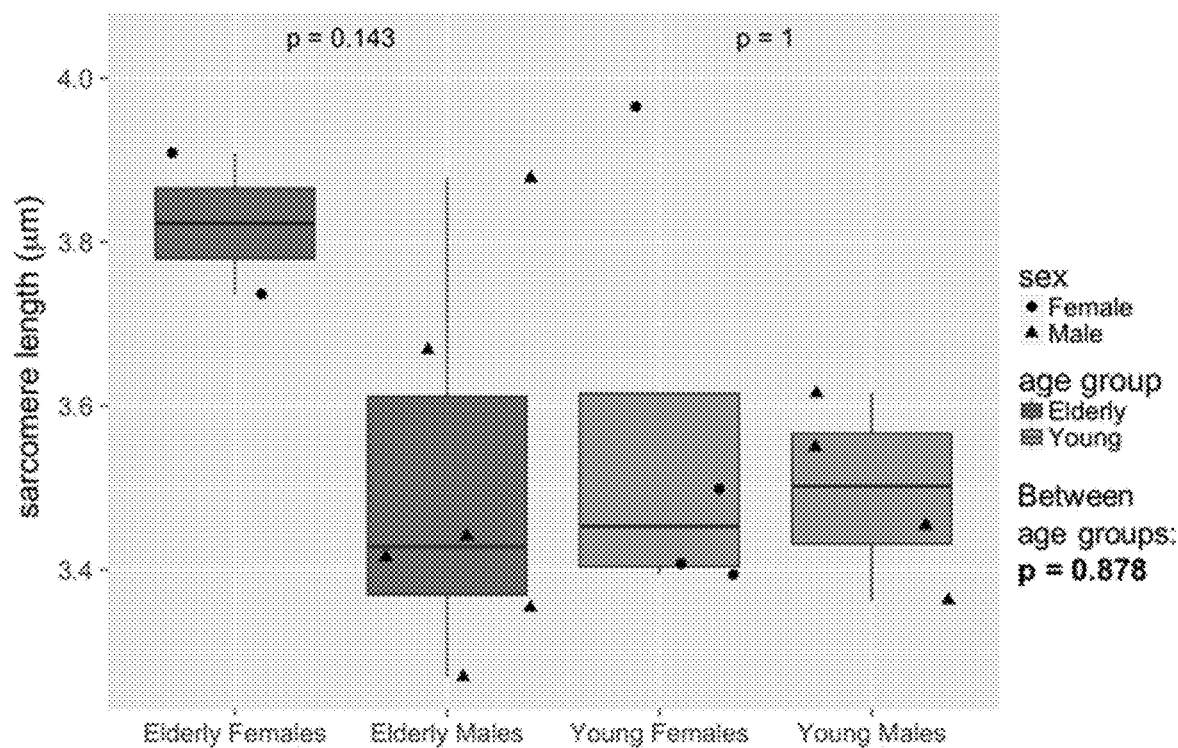
FIG. 20 shows average sarcomere length for young, elderly, male, and female subjects.

FIG. 20 shows the sarcomere length for the four subject groups measured during static imaging. Sarcomere length is seen to be similar between the four groups.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An apparatus for identifying or analyzing a muscle tissue of a subject, comprising:
   a light source for generating a beam of light;
   a first probe configured to transmit said beam of light from said light source to said muscle tissue of said subject, wherein upon contacting said muscle tissue, said beam of light generates at least one signal intrinsic to a property of said muscle tissue, and wherein said first probe is configured to receive said at least one signal intrinsic to said property of said muscle tissue;
   a collection unit in optical communication with said first probe, wherein said collection unit is configured to collect said at least one signal intrinsic to said property of said muscle tissue;
   a stimulation unit configured to locally stimulate said muscle tissue to generate local stimulation upon transmission of said beam of light to said muscle tissue, wherein said stimulation unit comprises at least one electrode in electrical communication with said first probe such that a circuit is formed between said at least one electrode and said first probe during said stimulation; and
   a computer controller operatively coupled to said light source and said collection unit, wherein said computer controller is programmed to
   (i) direct said light source to generate said beam of light, and
   (ii) process said at least one signal intrinsic to said property of said muscle tissue collected by said collection unit to generate at least one image of said muscle tissue, wherein said at least one image is usable to identify said muscle tissue of said subject.

2. The apparatus of claim 1, further comprising a second probe separate from said first probe, wherein said second probe is configured to receive at least one signal intrinsic to said property of said muscle tissue.

3. The apparatus of claim 2, wherein at least one of said first probe and said second probe comprises a needle.

4. The apparatus of claim 2, wherein said first probe and said second probe are separated by a distance of 5 millimeters or less.

5. The apparatus of claim 2, wherein each of said first probe and said second probe are configured to sense biologic electrical signals in a differential sensing arrangement.

6. The apparatus of claim 1, further comprising a telecentric objective in optical communication with said first probe.

7. The apparatus of claim 1, further comprising a dichroic mirror in optical communication with said first probe, wherein said dichroic mirror separates said beam of light from said at least one signal intrinsic to said property of said muscle tissue.

8. The apparatus of claim 1, wherein said computer controller is programmed to generate said at least one image in real time.

9. The apparatus of claim 1, wherein said at least one signal intrinsic to said property of said muscle tissue is a forward multiphoton microscopy (MPM) signal, a reverse MPM signal, an autofluorescence signal, or any combination thereof.

10. The apparatus of claim 1, wherein one of said at least one electrode and said first probe is an anode and the other of said at least one electrode and said first probe is a cathode during said stimulation.

11. The apparatus of claim 1, wherein said at least one electrode comprises multiple electrodes.

12. The apparatus of claim 1, wherein said local stimulation is applied in pulses.

13. The apparatus of claim 1, wherein said first probe is configured to sense biologic electrical signals.

14. The apparatus of claim 1, wherein said at least one image is usable to identify a muscle disease in said muscle tissue.

15. The apparatus of claim 14, wherein said muscle disease is sarcopenia or a muscular degenerative disease.

16. The apparatus of claim 1, wherein said beam of light is a pulsed beam of light.

17. The apparatus of claim 1, wherein said beam of light comprises polarized light.

18. A method for identifying or analyzing a muscle tissue of a subject, comprising:
 (a) providing a probe set comprising a first probe;
 (b) transmitting a beam of light from a light source to said muscle tissue via said first probe, wherein upon contacting said muscle tissue, said beam of light generates at least one signal intrinsic to a property of said muscle tissue;
 (c) using said first probe to direct said at least one signal intrinsic to said property of said muscle tissue to a collection unit;
 (d) locally stimulating said muscle tissue with a stimulation unit upon transmission of said beam of light to said muscle tissue, wherein said stimulation unit comprises at least one electrode in electrical communication with said first probe such that a circuit is formed between said at least one electrode and said first probe during said stimulation; and
 (e) processing said at least one signal intrinsic to said property of said muscle tissue collected by said collection unit to generate at least one image of said muscle tissue, wherein said at least one image is usable to identify said muscle tissue of said subject.

19. The method of claim 18, wherein said at least one signal intrinsic to said property of said muscle tissue is a forward multiphoton microscopy (MPM) signal, a reverse MPM signal, an autofluorescence signal, or any combination thereof.

20. The method of claim 18, wherein stimulating said muscle tissue comprises directionally stimulating said muscle tissue.

21. The method of claim 18, wherein said at least one image is generated in real time.

* * * * *